United States Patent
Hah et al.

(10) Patent No.: US 10,605,810 B2
(45) Date of Patent: Mar. 31, 2020

(54) PINCERS COMPRISING ANTIBODY AND APTAMER CONJUGATED VIA A LINKER WHICH BINDS TO THE SAME TARGET MATERIAL AND USE THEREOF

(71) Applicant: University-Industry Cooperation Group Of Kyung Hee University, Gyeonggi-do (KR)

(72) Inventors: Sang Soo Hah, Gyeonggi-do (KR); Sung Muk Kang, Gyeonggi-do (KR)

(73) Assignee: University-Industry Cooperation Group of Kyung Hee University, Gyeonggi-do (KR)

(*) Notice: Subject to any disclaimer, the term of this patent is extended or adjusted under 35 U.S.C. 154(b) by 169 days.

(21) Appl. No.: 15/108,753

(22) PCT Filed: Dec. 26, 2014

(86) PCT No.: PCT/KR2014/012892
§ 371 (c)(1),
(2) Date: Jun. 28, 2016

(87) PCT Pub. No.: WO2015/102316
PCT Pub. Date: Jul. 9, 2015

(65) Prior Publication Data
US 2017/0028070 A1 Feb. 2, 2017

(30) Foreign Application Priority Data
Dec. 30, 2013 (KR) .................... 10-2013-0167768

(51) Int. Cl.
| | |
|---|---|
| *G01N 33/573* | (2006.01) |
| *G01N 33/53* | (2006.01) |
| *G01N 33/536* | (2006.01) |
| *A61K 47/68* | (2017.01) |
| *A61K 47/54* | (2017.01) |
| *C07K 16/00* | (2006.01) |
| *C07K 16/36* | (2006.01) |
| *C07K 16/32* | (2006.01) |
| *C07K 16/46* | (2006.01) |
| *C12N 15/10* | (2006.01) |
| *C12N 15/115* | (2010.01) |

(52) U.S. Cl.
CPC ......... *G01N 33/573* (2013.01); *A61K 47/549* (2017.08); *A61K 47/6809* (2017.08); *A61K 47/6851* (2017.08); *A61K 47/6855* (2017.08); *C07K 16/00* (2013.01); *C07K 16/32* (2013.01); *C07K 16/36* (2013.01); *C07K 16/468* (2013.01); *C12N 15/1048* (2013.01); *C12N 15/115* (2013.01); *G01N 33/536* (2013.01); *G01N 33/5308* (2013.01); *C07K 2317/31* (2013.01); *C07K 2317/73* (2013.01); *C07K 2317/77* (2013.01); *C07K 2317/92* (2013.01); *C12N 2310/16* (2013.01); *C12N 2310/3513* (2013.01); *C12N 2320/32* (2013.01); *G01N 2333/91205* (2013.01); *G01N 2333/974* (2013.01)

(58) Field of Classification Search
None
See application file for complete search history.

(56) References Cited

U.S. PATENT DOCUMENTS

| | | | | |
|---|---|---|---|---|
| 2009/0123467 | A1* | 5/2009 | Bedi .................. | A61K 47/6807 424/134.1 |
| 2011/0052697 | A1* | 3/2011 | Farokhzad ........... | A61K 31/337 424/486 |

FOREIGN PATENT DOCUMENTS

| | | | | |
|---|---|---|---|---|
| KR | 2008-0097995 | | 11/2008 | |
| KR | 10-2011-0008086 | * | 1/2011 | ........... A61K 39/395 |
| WO | WO 2009/126920 | * | 10/2009 | ........... A61K 39/395 |

OTHER PUBLICATIONS

Liu, et al., "Novel HER2 Aptamer Selectively Delivers Cytotoxic Drug to HER2-positive Breast Cancer Cells in Vitro", Journal of Translational Medicine, 2012, 10:145 pp. 1-10.
(Continued)

*Primary Examiner* — Nelson B Moseley, II
(74) *Attorney, Agent, or Firm* — Cesari and McKenna, LLP

(57) ABSTRACT

The present invention relates to a pincer for binding to a target material, wherein an antibody or a fragment thereof binding to a first target site of the target material and an aptamer binding to a second target site are conjugated via a linker, a preparation method thereof, a composition for detecting or separating the target material comprising the pincer, a kit for detecting or separating the target material comprising the composition, and a method for detecting or separating the target material using the kit.

Also, the present invention relates to a drug carrier comprising the pincer for binding to a target material, wherein an aptamer conjugated to a second target site of the pincer loads the drug.

The antibody-aptamer pincer comprising the antibody and the aptamer, which target for the different binding sites on the same material of the present invention shows a ten- to hundred-fold increased binding affinity for the target molecule compared to using the antibody or the aptamer alone, and thus can be usefully applied for detection and/or separation of traces of the target material.

Further, the affinity of the drug carrier prepared by the binding of the antibody with the aptamer for the target molecule is increased, and thus, it can be used as a drug carrier against harmful tumors.

10 Claims, 17 Drawing Sheets
Specification includes a Sequence Listing.

(56) References Cited

OTHER PUBLICATIONS

Luo, et al., "Dimers and multimers of monoclonal IgG I exhibit higher in vitro binding affinities to Fcγ receptors", mAbs 1:5, 491-504, 2009.

Kang, et al., "Improved Ligand Binding by Antibody-Aptamer Pincers" Bioconjugate Chemistry, 2014, 25, pp. 1421-1427.

* cited by examiner

[FIG. 1]
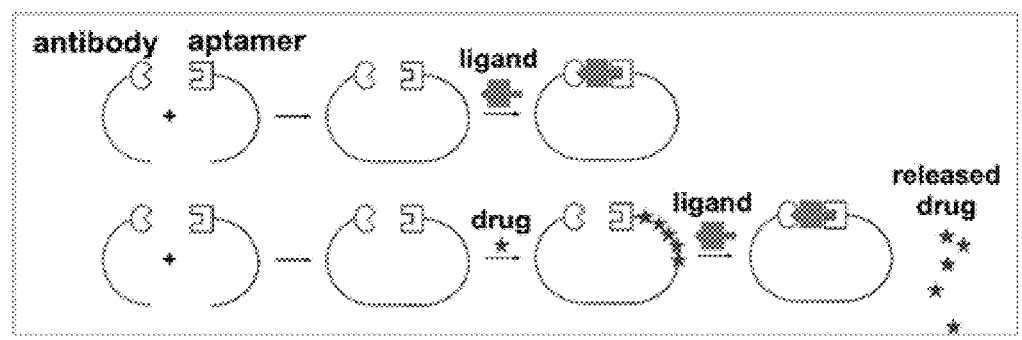

[FIG. 2]
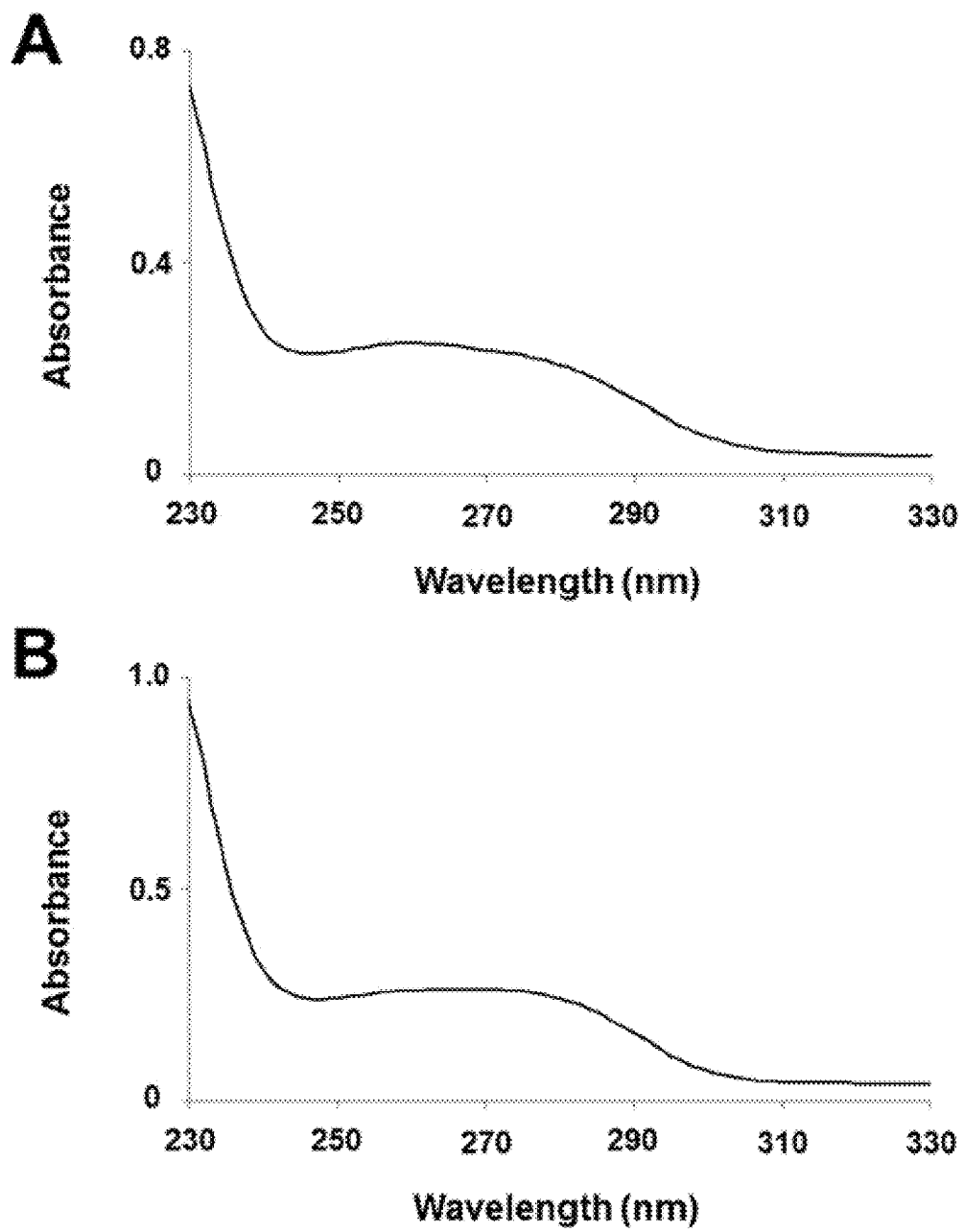

【FIG. 3】
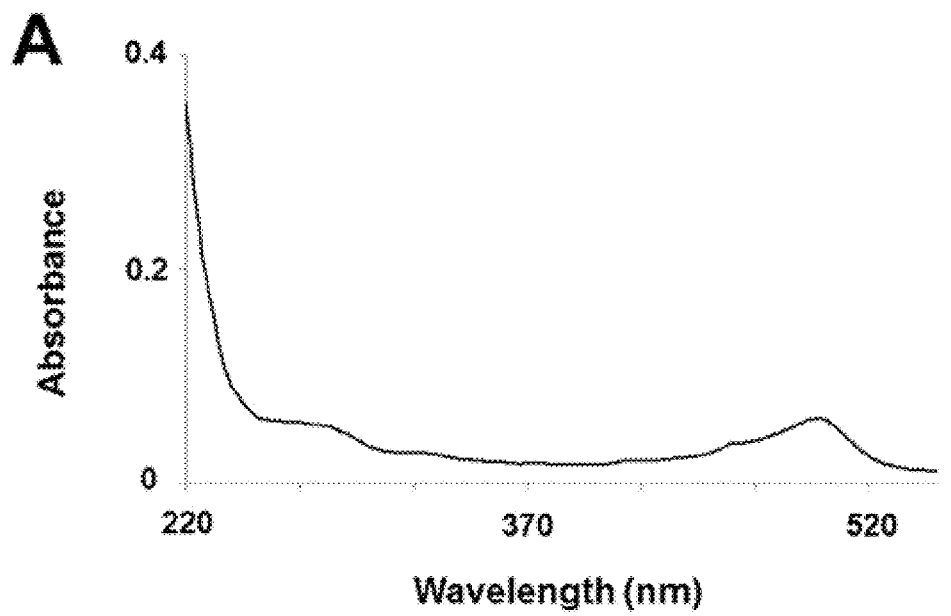
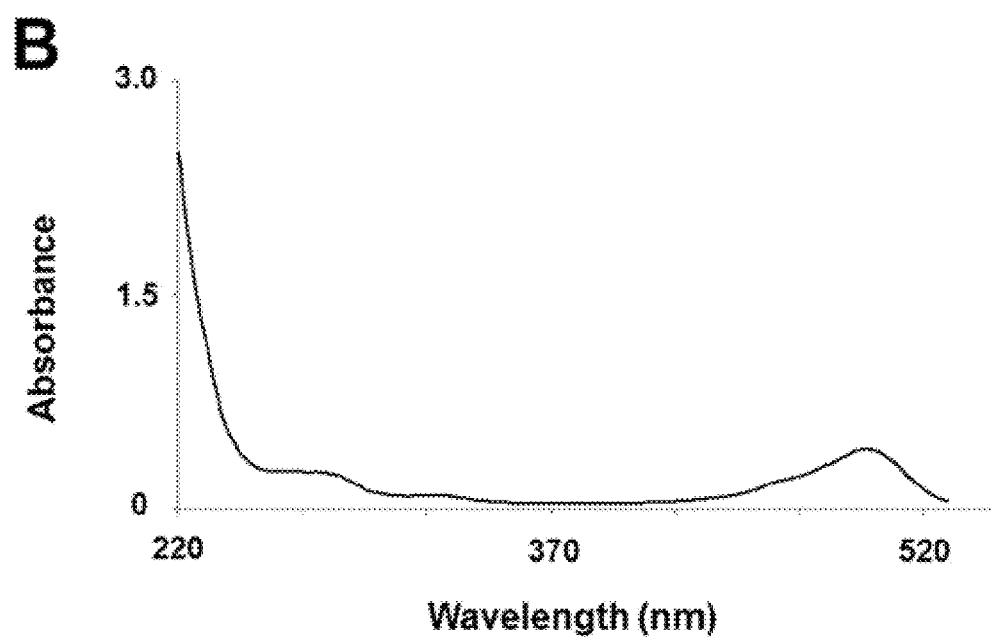

[FIG. 4]
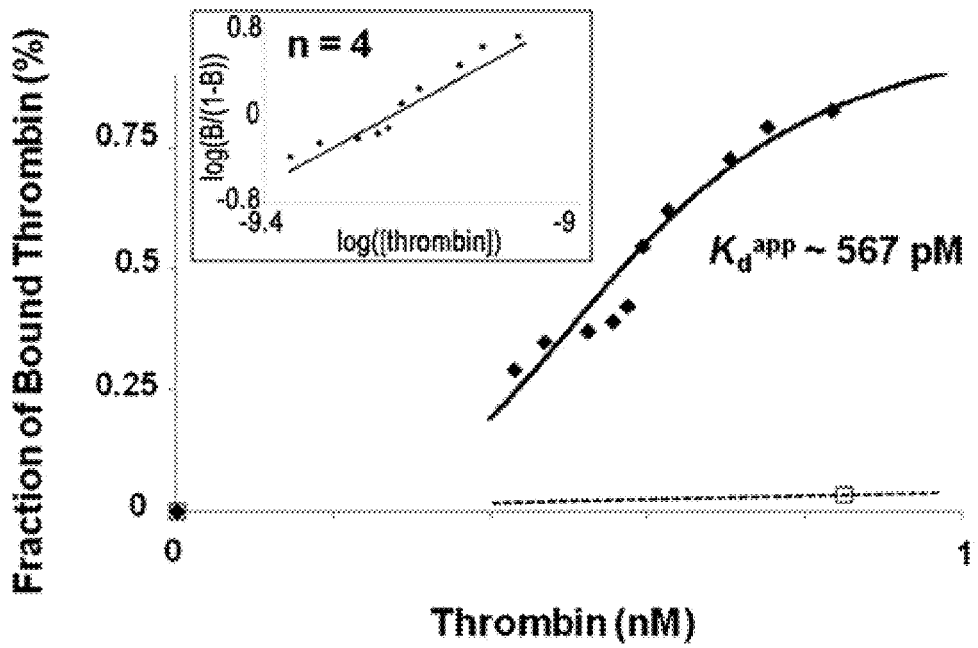
[FIG. 5]
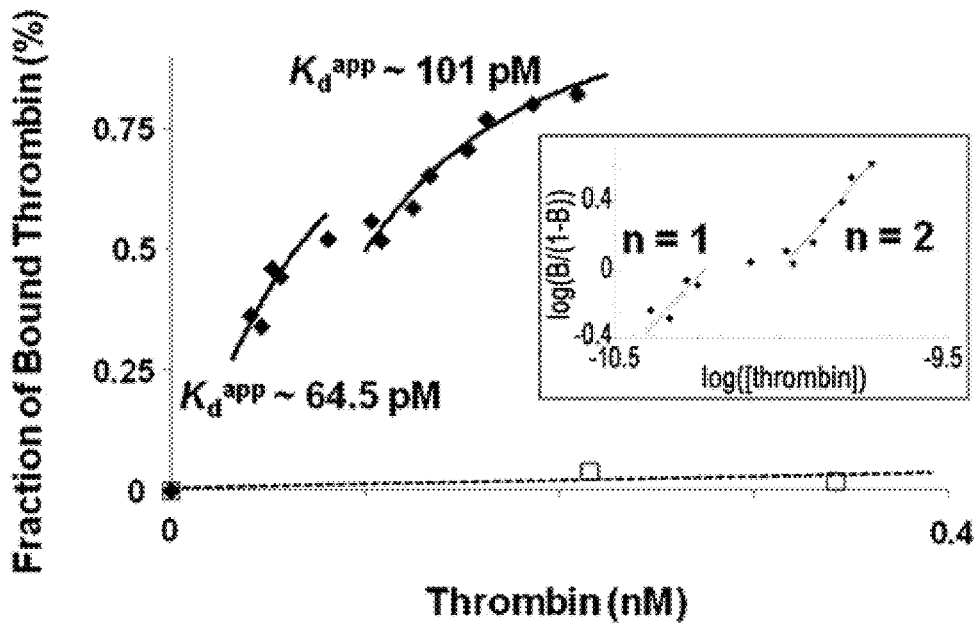

[FIG. 6a]
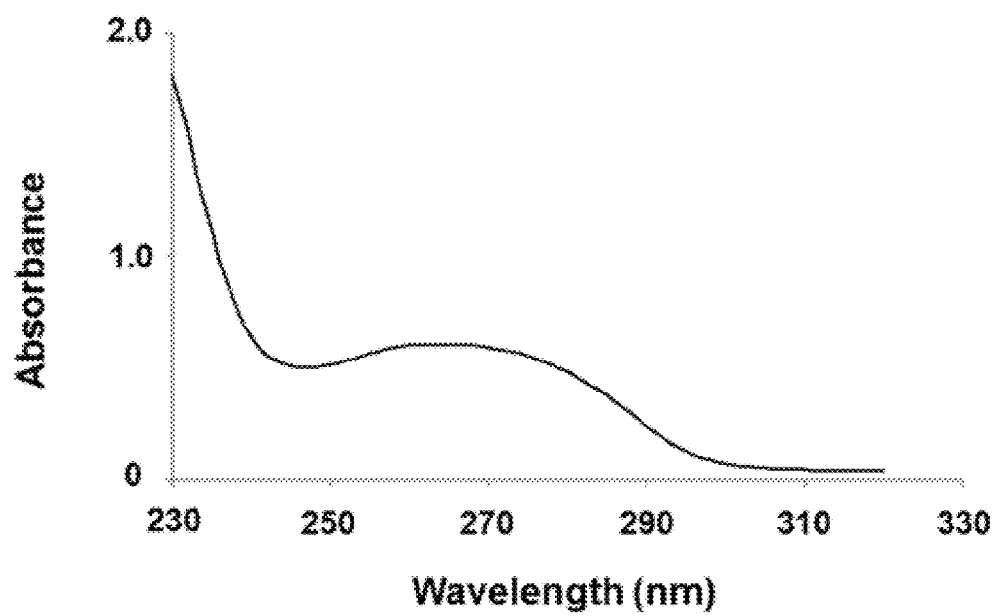
[FIG. 6b]
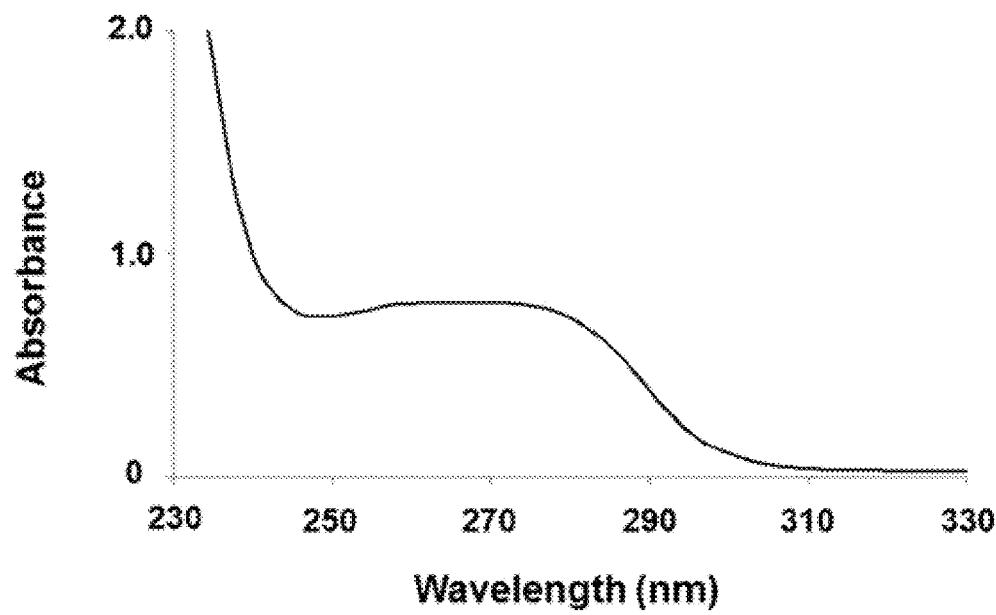

[FIG. 6c]
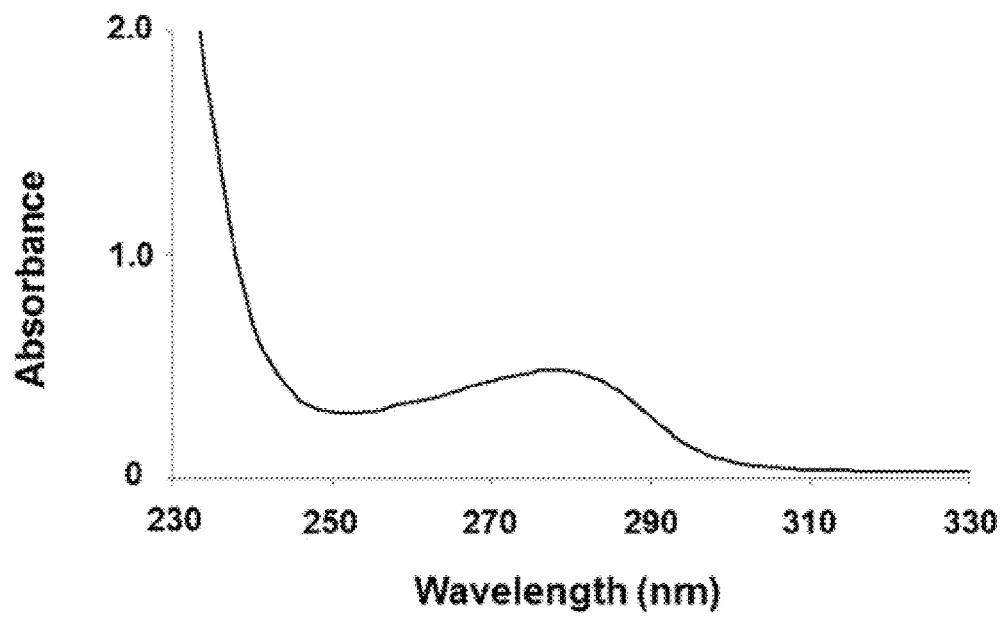
[FIG. 6d]
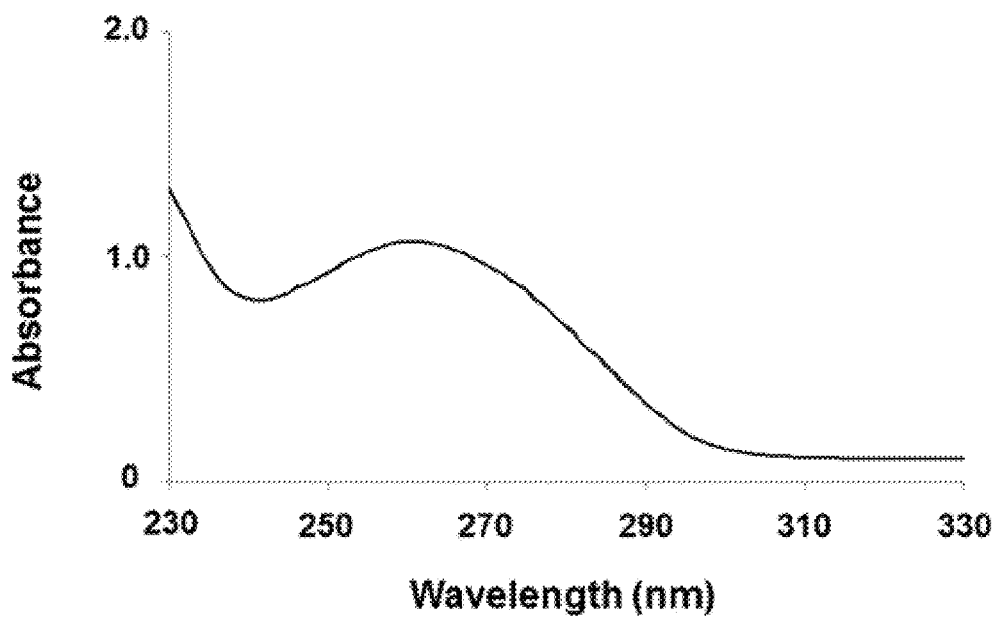

[FIG. 7a]
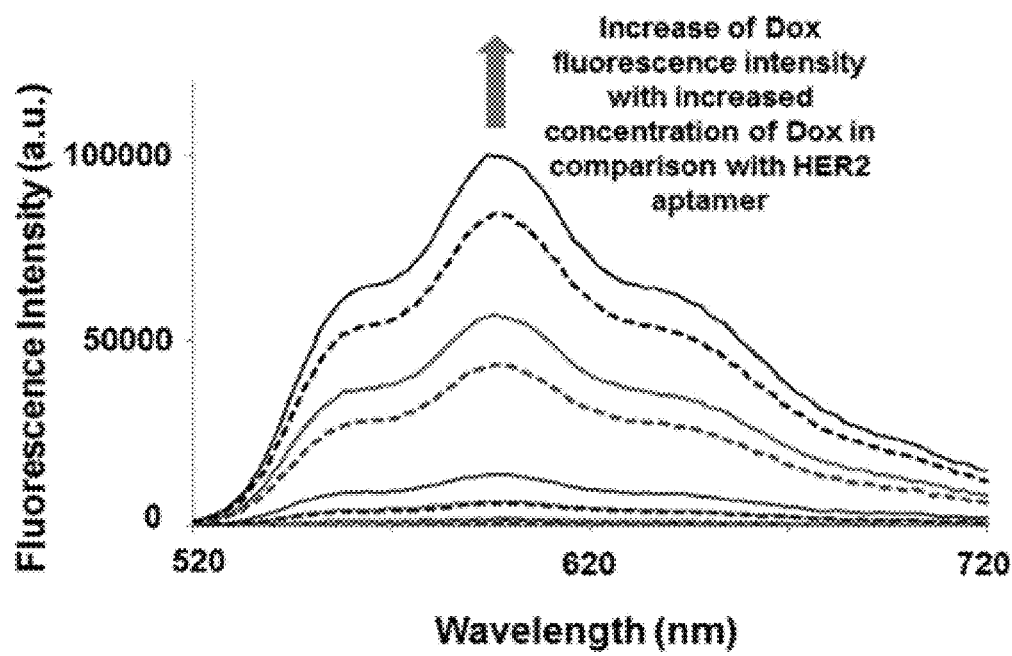
[FIG. 7b]
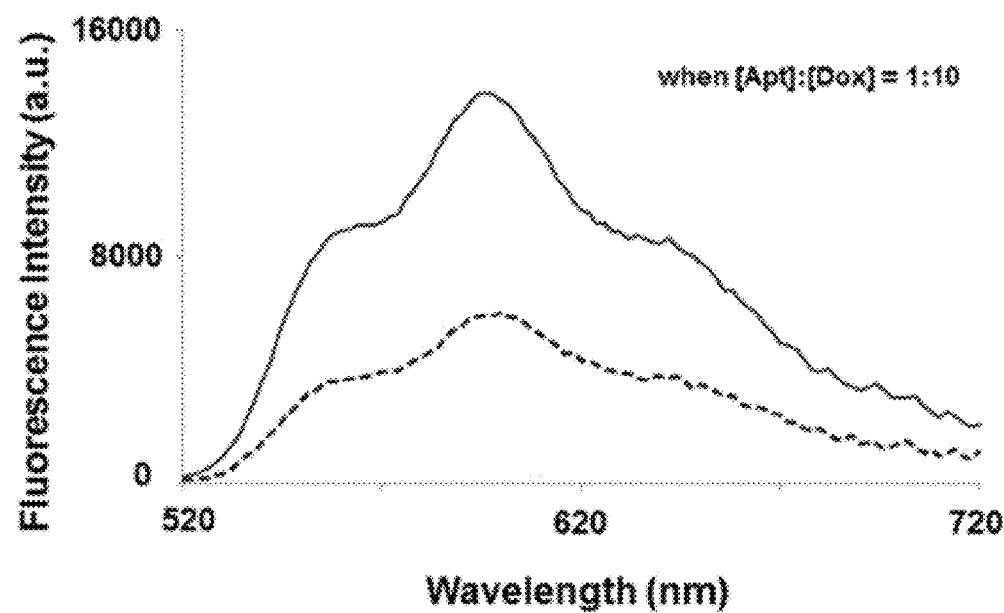

[FIG. 7c]
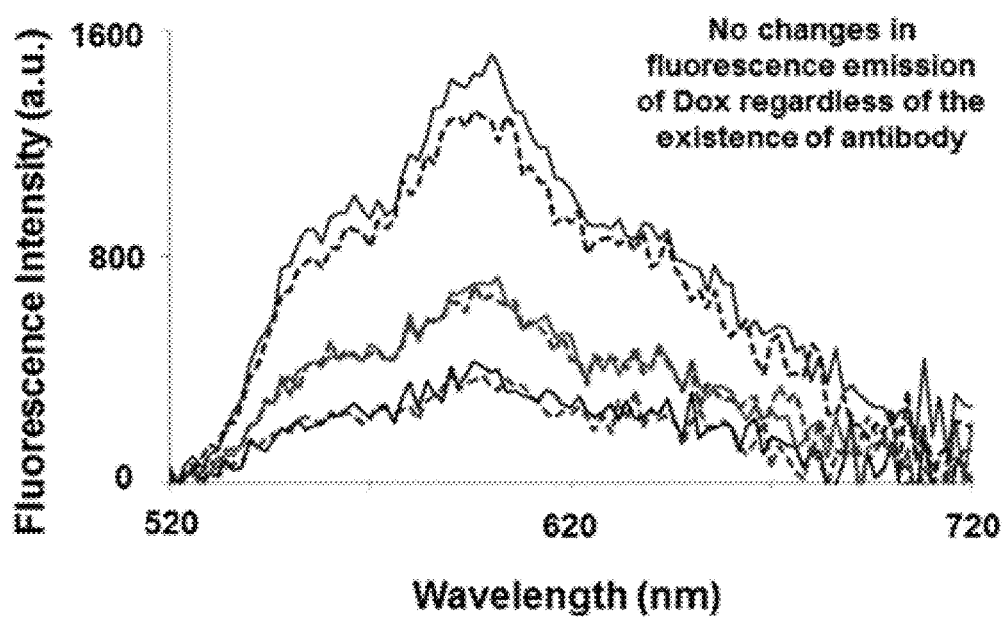
[FIG. 7d]
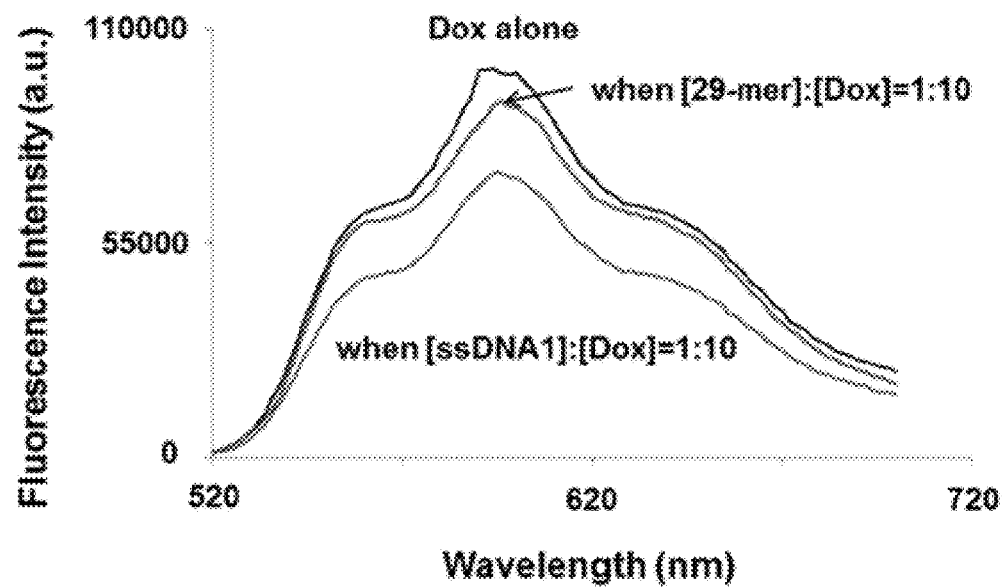

[FIG. 8]
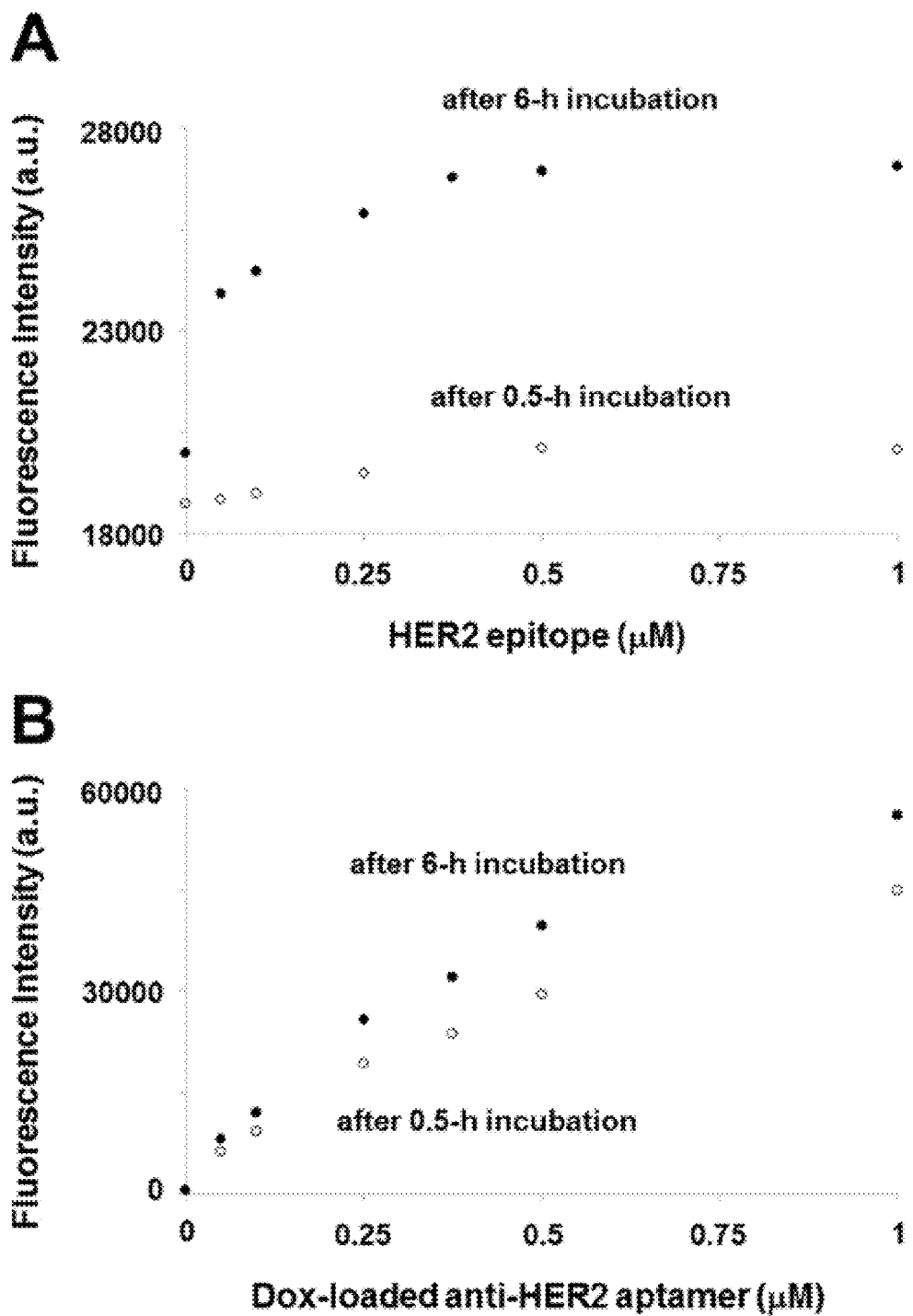

[FIG. 9]
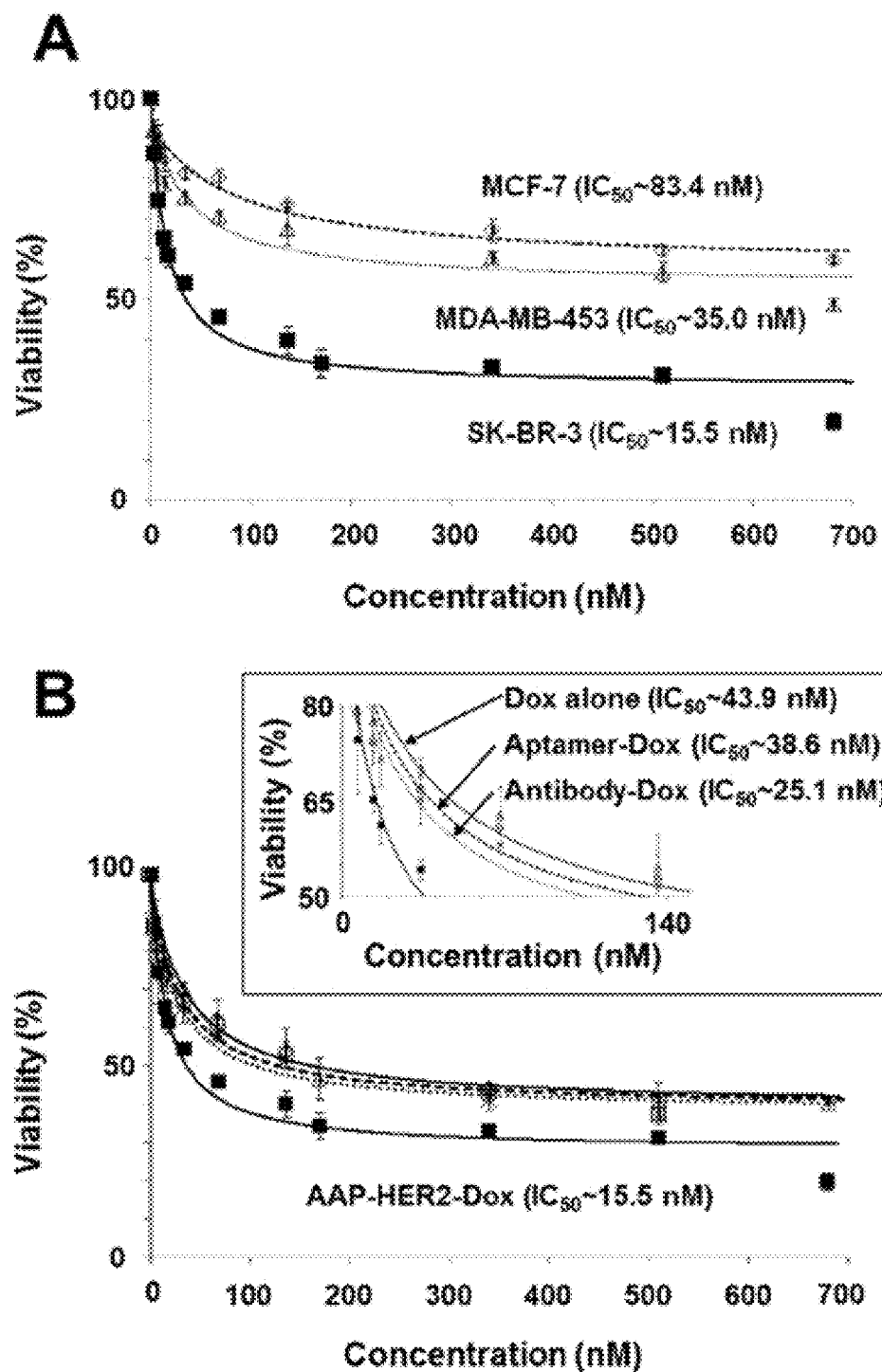

[FIG. 10]
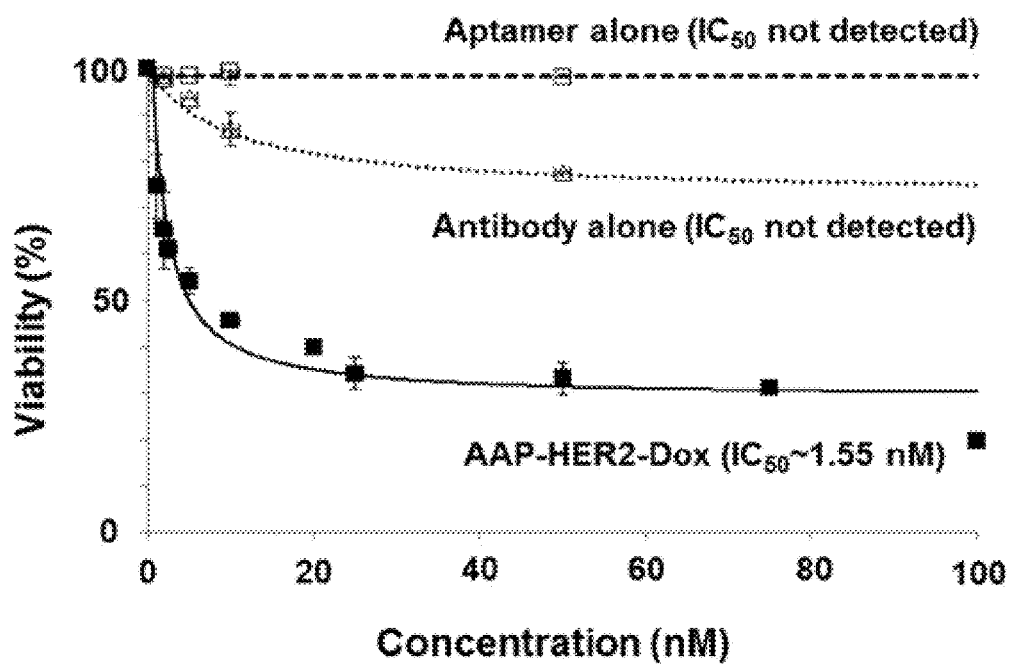

[FIG. 11]
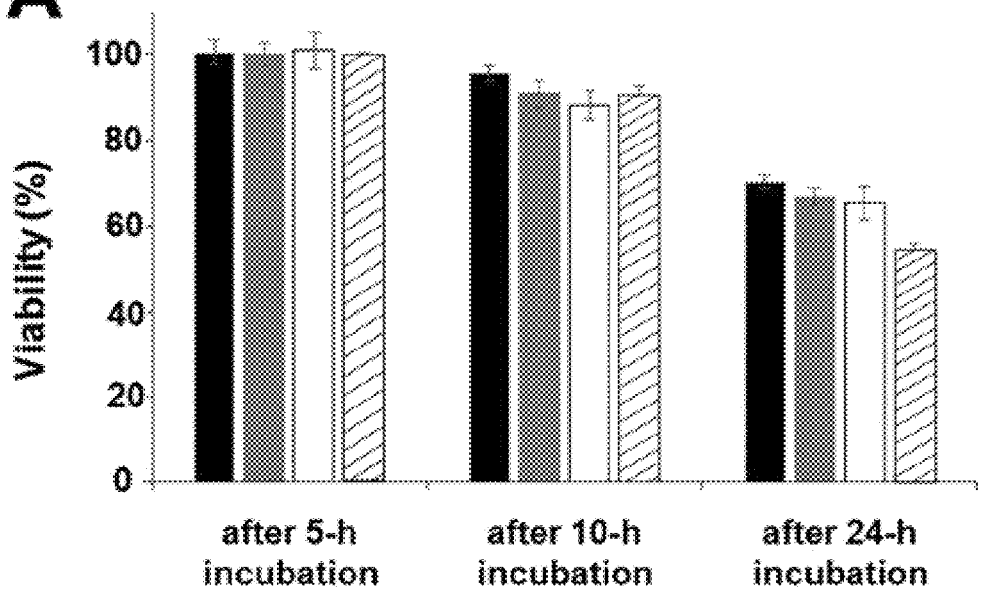
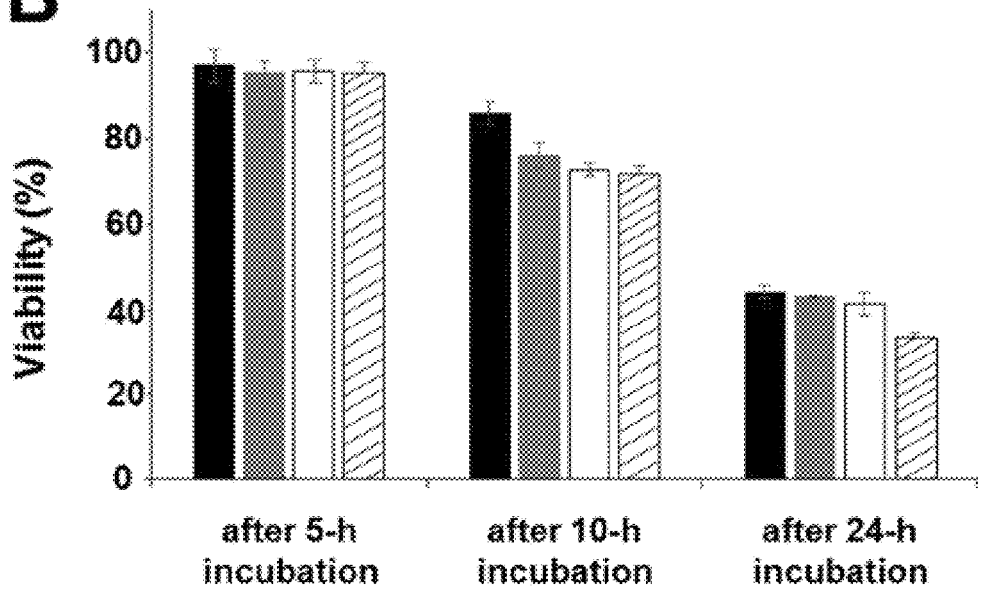

[FIG. 12a]
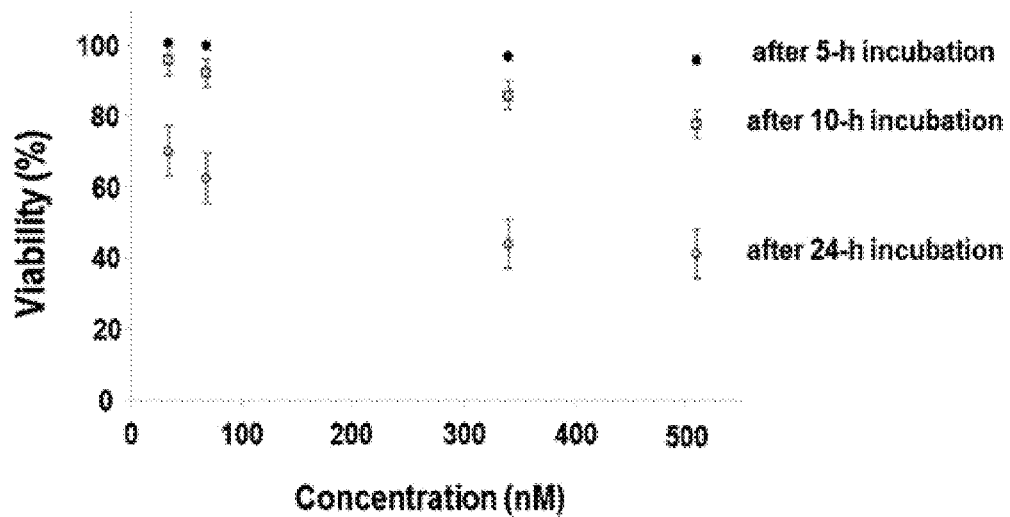
[FIG. 12b]
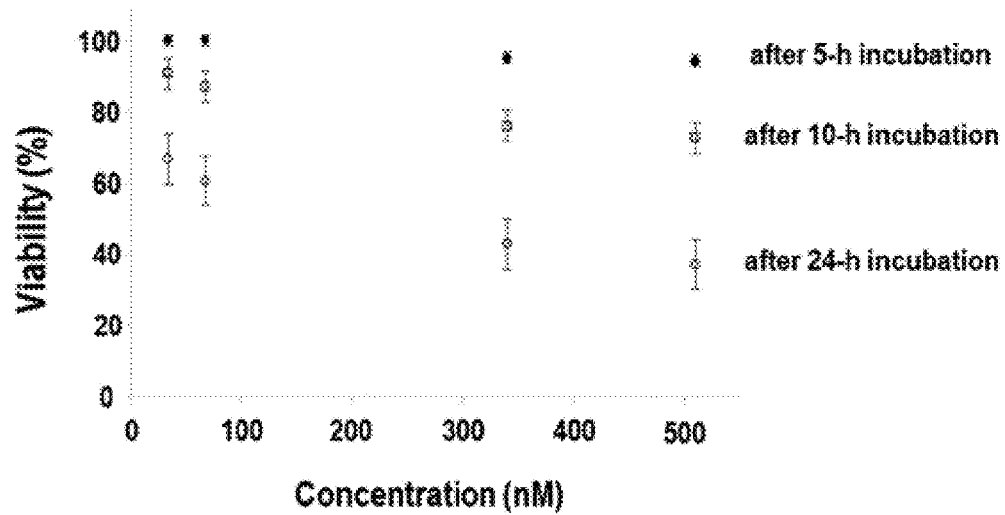

【FIG. 12c】
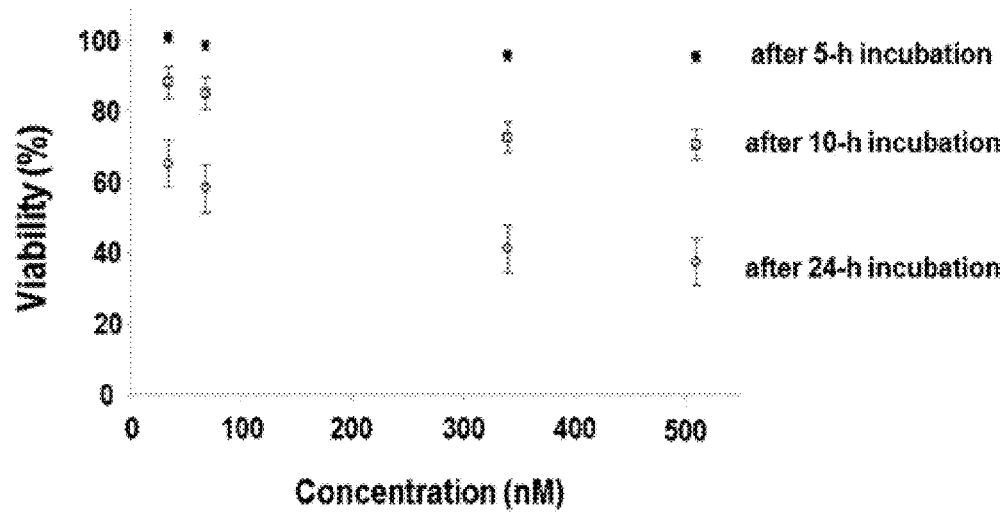
【FIG. 12d】
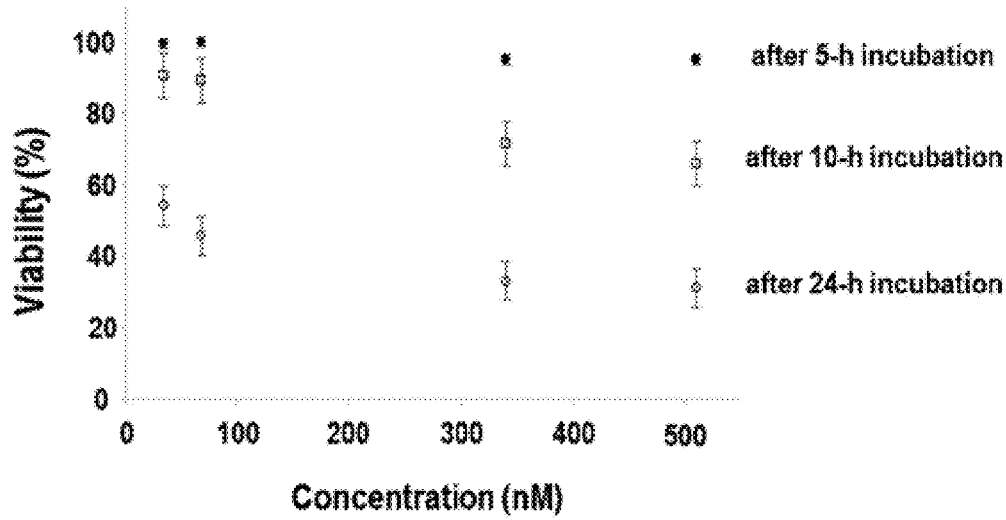

[FIG. 13]
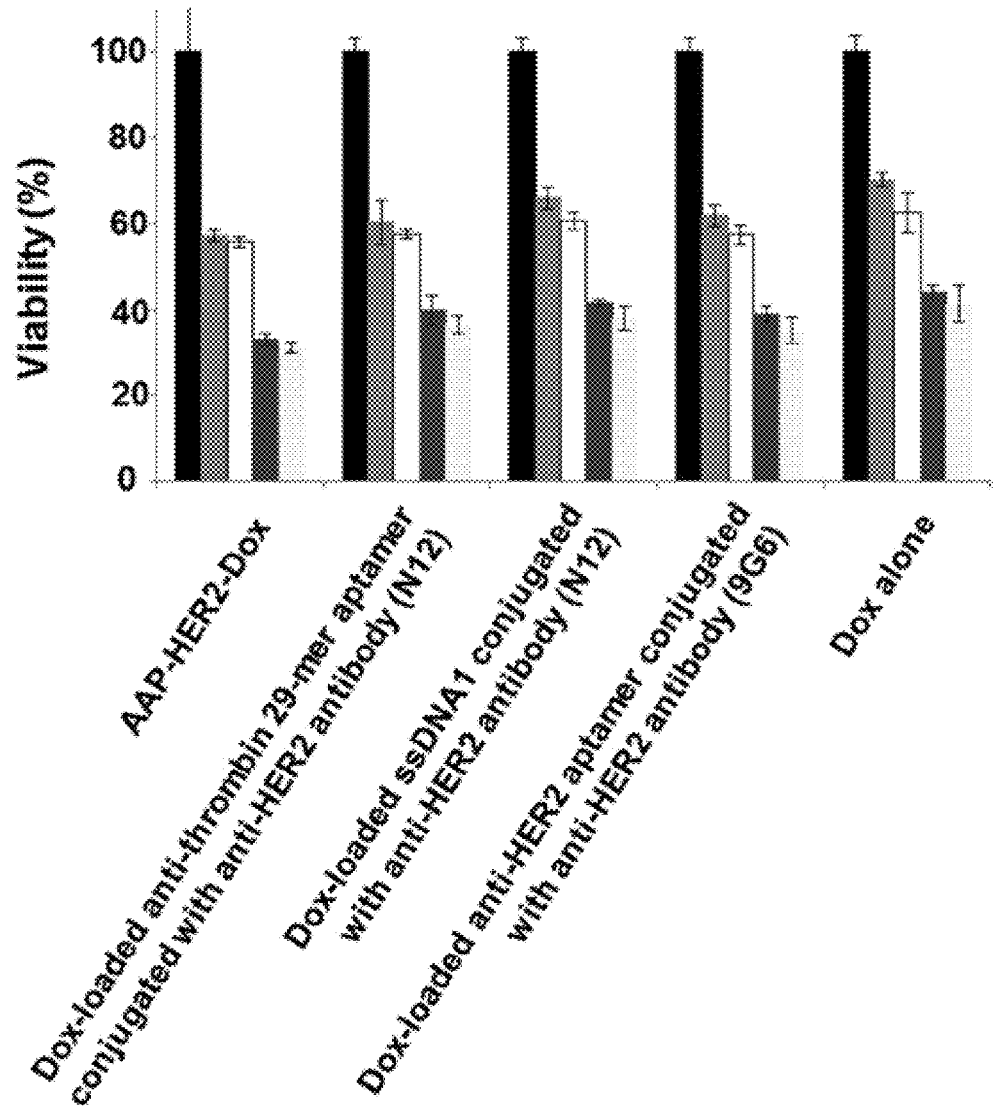

[FIG. 14]
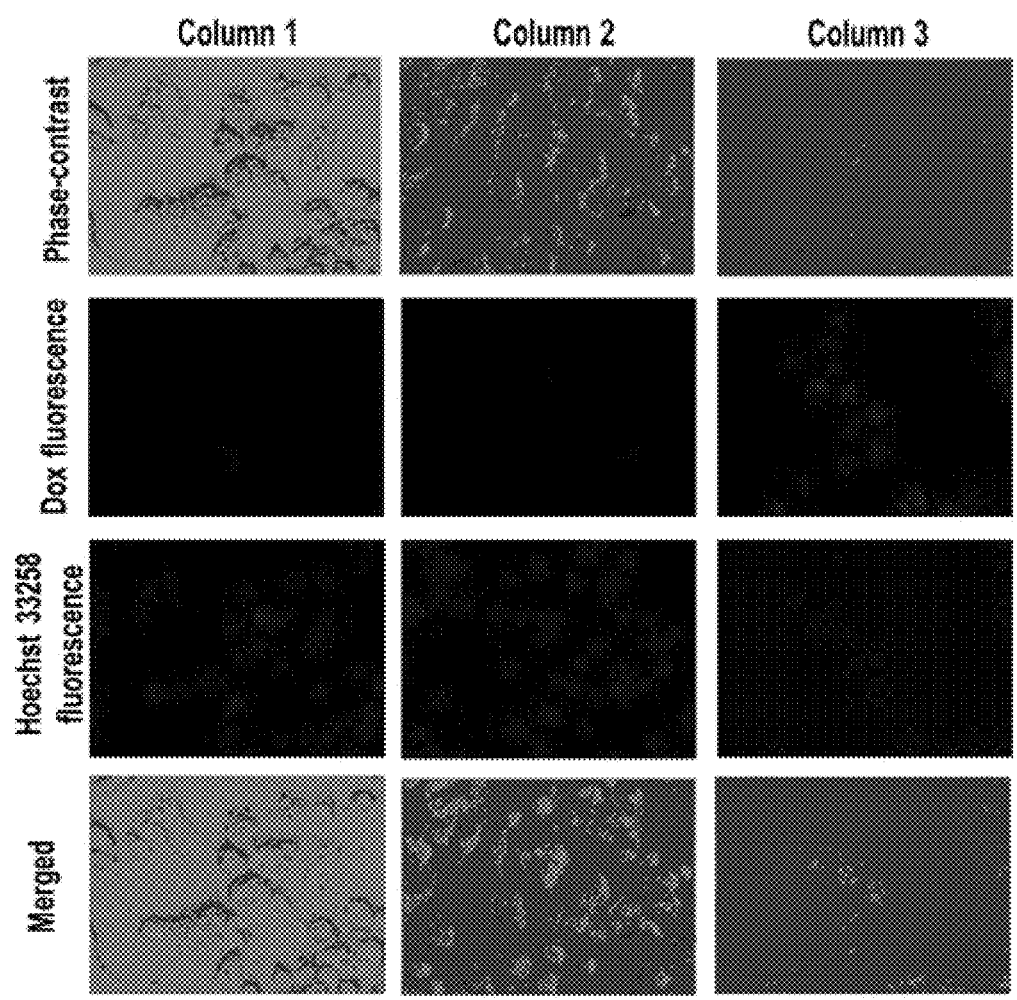

[FIG. 15]
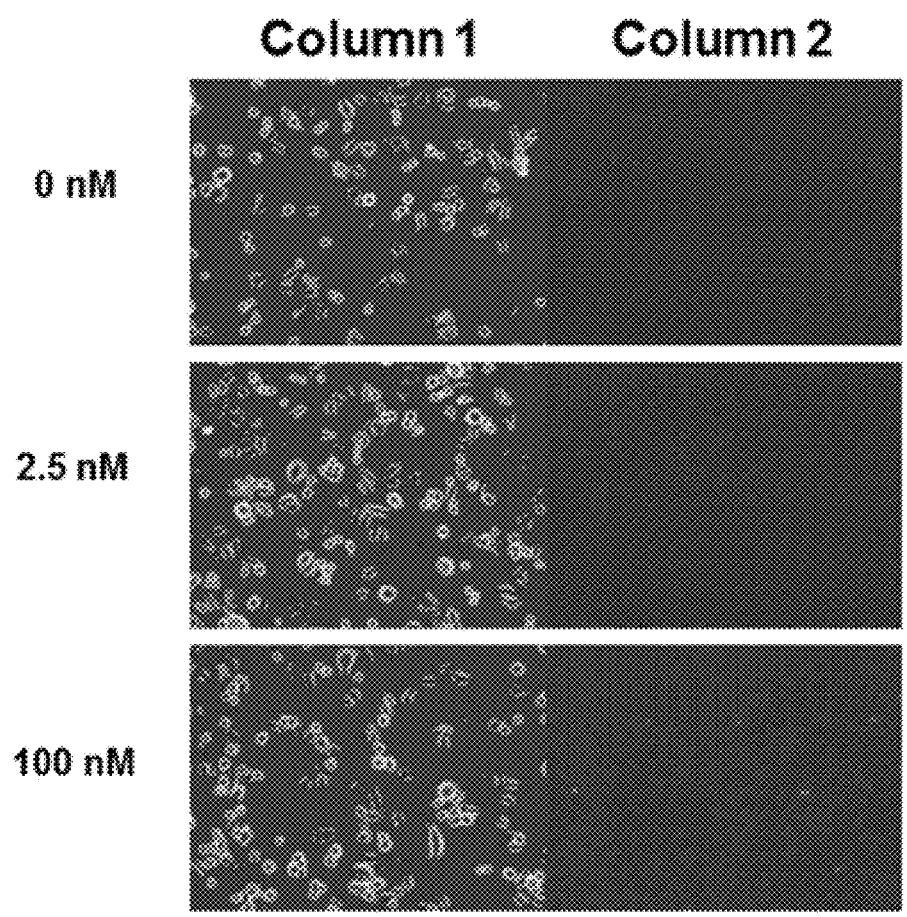

SEQUENCE LISTING

```
<160> NUMBER OF SEQ ID NOS: 3

<210> SEQ ID NO 1
<211> LENGTH: 15
<212> TYPE: DNA
<213> ORGANISM: Artificial sequence
<220> FEATURE:
<223> OTHER INFORMATION: 15mer aptamer
<220> FEATURE:
<221> NAME/KEY: variation
<222> LOCATION: (1)..(1)
<223> OTHER INFORMATION: Guanine is modified by attaching H2N-(CH2)6

<400> SEQUENCE: 1
ggttggtgtg gttgg                                                     15

<210> SEQ ID NO 2
<211> LENGTH: 29
<212> TYPE: DNA
<213> ORGANISM: Artificial sequence
<220> FEATURE:
<223> OTHER INFORMATION: 29mer aptamer
<220> FEATURE:
<221> NAME/KEY: variation
<222> LOCATION: (1)..(1)
<223> OTHER INFORMATION: Adenine is modified by attaching H2N-(CH2)6

<400> SEQUENCE: 2
agtccgtggt agggcaggtt ggggtgact                                      29

<210> SEQ ID NO 3
<211> LENGTH: 86
<212> TYPE: DNA
<213> ORGANISM: Artificial sequence
<220> FEATURE:
<223> OTHER INFORMATION: HER2 aptamer
<220> FEATURE:
<221> NAME/KEY: variation
<222> LOCATION: (1)..(1)
<223> OTHER INFORMATION: Adenine is modified by attaching H2N-(CH2)6

<400> SEQUENCE: 3
aaccgcccaa atccctaaga gtctgcactt gtcattttgt atatgtattt ggttttggc     60 tctcacagac acactacaca cgcaca                                         86
```

PINCERS COMPRISING ANTIBODY AND APTAMER CONJUGATED VIA A LINKER WHICH BINDS TO THE SAME TARGET MATERIAL AND USE THEREOF

CROSS REFERENCE TO RELATED APPLICATIONS

This application is the National Stage of International Application No. PCT/KR2014/012892, filed on Dec. 26, 2014, which claims priority to Korean Application No. 10-2013-0167768, filed on Dec. 30, 2013. The contents of both applications are hereby incorporated by reference in their entirety.

TECHNICAL FIELD

The present invention relates to a pincer for binding to a target material, wherein an antibody or a fragment thereof binding to a first target site of the target material and an aptamer binding to a second target site of the target material are conjugated via a linker, a preparation method thereof, a composition for detecting or separating the target material comprising the pincer, a kit for detecting or separating the target material comprising the composition, a method for detecting or separating the target material using the kit, and a drug carrier wherein the drug is loaded onto the pincer.

BACKGROUND ART

Antibodies (Ab), which are proteins also known as immunoglobulins (Ig), are large Y-shaped proteins produced from B cells, which are used by the immune system to identify and neutralize foreign objects such as viruses or bacteria. The antibodies are substances that recognize a specific part of foreign targets, called antigens, and specifically bind thereto to induce an antigen-antibody reaction. Due to the specific binding between the antigen and antibody, the antibodies are not only used to detect antigens, but are also used to diagnose and treat diseases. There has been a report on antibody dimerization as a method for improving the binding affinity for such target materials (Luo, Y. et al., mAbs. 2009, 1(5): 491-504). However, the antibodies not only show low expression levels and low solubility and must employ animal cell expression cell lines, but also show disadvantages of high purification costs, a reduced stability in reducing environments, etc. Therefore, efforts are actively being made to discover substances which can specifically bind to target materials in replacement of the antibodies.

Meanwhile, aptamers are specific types of single-stranded nucleic acids (DNA, RNA, or modified nucleic acids), which have stable three-dimensional structures themselves and can bind to target materials with high affinity and specificity. The aptamers can be obtained via Systematic Evolution of Ligands by Exponential Enrichment (SELEX) from a nucleic acid library with random sequences.

Such aptamers are considered as good alternatives for antibodies, and a large number of aptamers are known to bind to metal ions, small chemical molecules, proteins, and even cells specific enough that they have a dissociation constant at the level of nanomoles to picomoles. Also, the aptamers show advantageous characteristics over the antibodies as follows through specific experimentations. The first characteristic is that the aptamers can be obtained from a nucleic acid library such that the aptamers can target certain molecules (from small inorganic ions to cells). This characteristic enables the aptamers to overcome the limitation that the antibodies must be obtained from cells or animals. The second characteristic is that the aptamers selected from the library can be amplified via polymerase chain reaction (PCR) or transcribed in order to obtain a large amount of aptamers having high purity. The third characteristic is that functional groups on the aptamers can be easily modified if the aptamers are used for other purposes such as immobilization on a solid surface, etc., as the aptamers have relatively simple chemical structures. Lastly, the aptamers can be applied to chemical applications where slightly more extreme conditions are required (high temperatures or extreme pH) because the aptamers are much more stable than the antibodies. In addition, since the aptamers can be chemically produced from a large-scale synthesis, they are economically favorable and have a target affinity close to that of the antibodies. In contrast, the size of the aptamers is significantly smaller than that of the antibodies (about 1 to 2 nm).

DISCLOSURE

Technical Problem

The present inventors have made extensive efforts to invent a material which can detect and/or separate traces of a target material by showing significantly increased binding affinity for the target material compared to antibodies or aptamers. As a result, an antibody-aptamer pincer (AAP), wherein an antibody and an aptamer, which specifically bind to different binding sites on the same target molecule, are conjugated via a linker, shows significantly improved binding affinity for the target material compared to monoclonal antibodies or aptamers. Also, the present inventors discovered that the antibody-aptamer pincer shows excellent target localization and therapeutic effects (for example, anticancer activity) when a drug is loaded thereinto, thereby completing the present invention.

Technical Solution

One objective of the present invention is to provide a pincer for binding to a target material, wherein an antibody or a fragment thereof binding to a first target site of the target material and an aptamer binding to a second target site of the target material are conjugated via a linker.

Another objective of the present invention is to provide a method for preparing the pincer for binding to a target material comprising: preparing an antibody or a fragment thereof conjugated to a first linker and an aptamer conjugated to a second linker; and conjugating the antibody and the aptamer conjugated to the linkers via a covalent bond.

A further objective of the present invention is to provide a method for preparing the pincer for binding to a target material, comprising reacting a cross-linking agent comprising a first functional group at one end and a second functional group at another end with an antibody and an aptamer.

A still further objective of the present invention is to provide a composition for detecting or separating a target material comprising the pincer for binding to a target material.

A still further objective of the present invention is to provide a kit for detecting or separating a target material comprising the composition for detecting or separating a target material.

A still further objective of the present invention is to provide a method for detecting or separating a target material, comprising bringing the composition for detecting or separating a target material into contact with a sample comprising the target material.

A still further objective of the present invention is to provide a drug carrier comprising the pincer for binding to a target material, wherein an aptamer conjugated to a second target site of the pincer loads the drug.

Advantageous Effects

The antibody-aptamer pincer including an antibody and an aptamer which target for different binding sites on the same material of the present invention shows a ten- to hundred-fold increased binding affinity for the target molecule compared to using the antibody or aptamer alone, and thus can be usefully applied for detection and/or separation of traces of the target material.

Further, the affinity of the drug carrier prepared by the binding of the drug with the aptamer for the target molecule is increased, and thus, it can be used as a drug carrier against harmful tumors.

BRIEF DESCRIPTION OF DRAWINGS

FIG. 1 is a schematic diagram showing an application of the antibody-aptamer pincer to a drug delivery and release system, and the operation principle thereof.

FIG. 2 shows UV absorption spectra of thrombin aptamers conjugated to anti-thrombin antibodies, specifically showing UV absorption spectra of (a) an anti-thrombin antibody conjugated to a thrombin 15-mer aptamer (AAA-15) and (b) an anti-thrombin antibody conjugated to an anti-thrombin 29-mer aptamer (AAA-29).

FIG. 3 shows UV absorption spectra of (a) FAM-labeled thrombin (508 nM) and (b) FAM-labeled bovine serum albumin (BSA, 2.632 μM).

FIG. 4 shows binding characteristics of thrombin for the anti-thrombin antibody conjugated to the anti-thrombin aptamer according to one embodiment of the present invention.

FIG. 5 shows binding characteristics of thrombin for the anti-thrombin antibody conjugated to the anti-thrombin 29-mer aptamer according to one embodiment of the present invention.

FIG. 6a shows UV absorption spectra of an anti-HER2 antibody conjugated to an anti-HER2 aptamer (AAP-HER2).

FIG. 6b shows UV absorption spectra of an anti-HER2 antibody conjugated to an anti-thrombin 29-mer aptamer.

FIG. 6c shows UV absorption spectra of an anti-HER2 antibody conjugated to single-stranded DNA 1 (ssDNA1).

FIG. 6d shows UV absorption spectra of an anti-HER2 antibody conjugated to an anti-HER2 aptamer (9G6).

FIG. 7a shows fluorescence spectrum analyses of the anti-HER2 aptamer and the anti-HER2 antibody in the presence of Dox: shows preparation of Dox solutions of varying concentrations by increasing the mole ratio of Dox (from bottom to top: 0.5, 1, 4, 10, 50, and 100) while fixing the concentration of the anti-HER2 aptamer.

FIG. 7b shows fluorescence spectrum analyses of the anti-HER2 aptamer and the anti-HER2 antibody in the presence of Dox: shows fluorescence intensity when the mole ratio of Dox/anti-HER2 aptamer is 10.

FIG. 7c shows preparation of Dox solutions of varying concentrations by increasing the mole ratio of Dox (from bottom to top: 1, 2, and 4) while fixing the concentration of the anti-HER2 antibody.

FIG. 7d shows fluorescence intensity when Dox (5 nmol) is used alone (top), when the anti-thrombin 29-mer aptamer is mixed at 50 nmol (middle), and when ssDNA1 is mixed at 50 nmol (bottom), and these were used as negative control groups.

FIG. 8 shows fluorescence spectrum analyses of a Dox-loaded anti-HER2 aptamer in the presence of HER2 epitope peptides: (a) HER2 epitope solutions of varying concentrations were mixed with 250 nM of the anti-HER2 aptamer when the molar ratio of Dox was fixed at 10; and (b) various concentrations of the Dox-loaded anti-HER2 aptamer were mixed with 250 nM of the HER2 epitope peptides when the molar ratio of Dox was fixed at 10, and each fluorescence spectrum was obtained after 0.5 hours (empty circle) and 6 hours (filled circle), respectively.

FIG. 9 shows concentration-dependent cell viability for SK-BR-3. FIG. 9a shows the effect of the AAP-HER2-Dox on the viability of SK-BR-3, MDA-MB-453, and MCF-7 cells. FIG. 9b shows concentration-dependent cell viability for SK-BR-3 on the AAP-HER2-Dox, the antibody-Dox, the aptamer-Dox, and Dox.

FIG. 10 shows concentration-dependent cell viability for SK-BR-3 in the presence of the AAP-HER2-Dox, the anti-HER2 antibody, and the anti-HER2-aptamer. The SK-BR-3 cells were exposed to the AAP-HER2-Dox, the anti-HER2 antibody or the anti-HER2-aptamer at a concentration range of 0 nM to 100 nM FIG. 11 shows cell viability of SK-BR-3 according to time-dependent incubation of Dox alone (black), the aptamer-Dox (grey), the antibody-Dox (white), and the AAP-HER2-Dox (hatching). The concentrations of the total amount loaded and free Dox were (a) 34 nM and (b) 340 nM, respectively.

FIG. 12a shows cell viability of SK-BR-3 according to time-dependent incubation in the presence of Dox alone. The cells were exposed to the total amount loaded and free Dox at the concentration range of 0 nM to 500 nM.

FIG. 12b shows cell viability of SK-BR-3 according to time-dependent incubation in the presence of the aptamer-Dox. The cells were exposed to the total amount loaded and free Dox at the concentration range of 0 nM to 500 nM.

FIG. 12c shows cell viability of SK-BR-3 according to time-dependent incubation in the presence of the antibody-Dox. The cells were exposed to the total amount loaded and free Dox at the concentration range of 0 nM to 500 nM.

FIG. 12d shows cell viability of SK-BR-3 according to time-dependent incubation in the presence of the AAP-HER2-Dox. The cells were exposed to the total amount loaded and free Dox at the concentration range of 0 nM to 500 nM. The cells were exposed to the total amount loaded and free Dox at the concentration range of 0 nM to 500 nM.

FIG. 13 shows concentration-dependent cell viability of SK-BR-3 cells in the presence of the AAP-HER2Dox, the Dox-loaded anti-thrombin 29-mer aptamer conjugated with the anti-HER2 antibody, the Dox-loaded ssDNA1 conjugated with the anti-HER2 antibody, the Dox-loaded anti-HER2 aptamer conjugated with the anti-HER2 antibody (9G6), and Dox alone.

FIG. 14 shows Dox release from SK-BR-3 cells treated with 100 nM of the aptamer-Dox (column 1), the antibody-Dox (column 2), and the AAP-HER2-Dox (column 3). The nuclei were stained by Hoechst 33258, and the images were confirmed after 4 hours of incubation.

FIG. 15 shows a microscopic image illustrating intracellular fluorescence release after 24-hour incubation of SK-BR-3 cells treated with the AAP-HER2-Dox (with Dox concentrations of 0 nM, 2.5 nM, and 100 nM) (Column 1:

BEST MODE FOR CARRYING OUT INVENTION

In a first aspect, the present invention provides a pincer for binding to a target material, wherein an antibody or a fragment thereof binding to a first target site of the target material and an aptamer binding to a second target site are conjugated via a linker.

As used herein, the term "pincer" is used to describe the characteristics of a complex where an antibody or a fragment thereof and an aptamer are conjugated via a linker. The complex, wherein an antibody or a fragment thereof binding to a first target site of the target material and an aptamer binding to a second target site are linked via a linker, binds to the same target material on different binding sites thereof, and thus it does not compete for the same target material, rather, it complementarily binds to the target material. Therefore, the pincer refers to a molecule with significantly improved binding affinity for the target material, and improved selectivity and sensitivity.

As used herein, the term "antibodies", which are proteins also known as immunoglobulin (Ig), refers to large Y-shaped proteins produced from B cells which are used to identify and neutralize foreign objects such as viruses or bacteria, and this is known as an immune response. Every foreign substance entering from the outside can elicit such immune response, and specifically, the immune response has evolved to effectively remove or inhibit microorganisms capable of developing infectious diseases. However, the immune response is not only triggered by microorganisms, but also by various types of chemicals, their own cells, or transplanted cells from the outside. In general, the substances which enter from the outside and induce various immune responses including production of antibodies are defined as antigens, and the immune responses refer to neutralization of the corresponding antigens by specifically binding to the same.

The antibodies include polyclonal antibodies, monoclonal antibodies, whole antibodies, and antibody fragments. Also, the term includes chimeric antibodies (e.g., humanized murine antibodies) and bivalent or bispecific molecules (e.g., bispecific antibodies), diabodies, tribodies, and tetrabodies. The term further includes single chain antibodies having a binding function to FcRn, scab, derivatives of antibody constant regions, and protein scaffold-based artificial antibodies. The whole antibodies have a structure consisting of two full length light chains and two full length heavy chains, and each light chain is linked to the heavy chain via a disulfide bond.

The whole antibodies include IgA, IgD, IgE, IgM, and IgG, and IgG is a subtype antibody consisting of IgG1, IgG2, IgG3, and IgG4. The antibody fragments refer to fragments having an antigen-binding function and include Fd, Fab, Fab', F(ab')2, Fv, etc. The Fd refers to a heavy chain region of the Fab fragment. The Fab, which has a structure consisting of variable regions of the light and heavy chains, a constant region of the light chain, and a first constant region of the heavy chain (CH1 domain), has a single antigen-binding site. The Fab' is different from Fab in that it has a hinge region consisting of one or more cysteine residues at the C-terminal of the CH1 domain of the heavy chain. The F(ab')2 antibody is formed as the cysteine residues of the hinge region form disulfide bonds. The Fv (variable fragment) refers to minimum antibody fragments consisting of only a heavy chain variable region and a light chain variable region. Double disulfide Fv (dsFv) connects the heavy chain variable region and the light chain variable region via a disulfide bond, and single-chain Fv (scFv) generally connects the heavy chain variable region and the light chain variable region by a peptide linker via a covalent bond. Such antibody fragments can be obtained from hydrolytic enzymes (for example, the Fab can be obtained by restriction cleavage of the whole antibody with papain, and the F(ab')2 fragment can be obtained by cleavage with pepsin), and preferably these can be constructed by gene recombination. The fragments of the antibody used for a pincer for the purpose of the present invention may be fragments containing paratopes, which specifically recognize antigens and bind thereto.

As used herein, the term "aptamers" refers to substances capable of specifically binding to a target material to be detected in a sample, and refer to single-stranded nucleic acids (DNA, RNA, or modified nucleic acids) having a stable three-dimensional structure themselves, and the presence of the target material in a sample can be detected through the binding. The preparation of aptamers can be achieved by determining and synthesizing the sequences of oligonucleotides having selectivity and high binding affinity for a target protein to be confirmed, followed by modifying an end or 3' end of the oligonucleotides to —SH, —COOH, —OH, or —$NH_2$ in order to facilitate the binding thereof to a functional group of a linker, according to a general preparation method of aptamers.

The aptamers for the purpose of the present invention may be DNA having an amine group (—$NH_2$) at one end as an example, but are not limited thereto.

Oligonucleotides which specifically bind to a target material using SELEX, which is an in vitro selection, can be used as aptamers capable of binding to the target material of the present invention. The SELEX is an in vitro selective method for searching single-chain DNA or RNA oligonucleotides that perform selective functions in various forms, enabling one to search for aptamers with a desired function from the oligonucleotides having different sequences of up to $10^{15}$ random populations, and herein, each oligonucleotide has an intrinsic three-dimensional structure with a desired function (for example, selective recognition for target materials), and the sequences of the oligonucleotides selected by repeated selection and a conventional molecular biological method are amplified. After going through such repeated selection and amplification, the oligonucleotides having selective binding for desired molecules or transition states of the chemical process ultimately account for most of the population. Further, the sequence of each aptamer finally obtained through such processes can be confirmed. A kit for automated SELEX is also available for purchase (for example, Biomek 2000 pipetting robot, Beckman Coulter (USA)).

The aptamers can be selected, without limitation, according to target materials, and may preferably be aptamers capable of binding to different binding sites while specifically binding to a target material identical to that conjugated with an antibody or a fragment thereof conjugated via a linker, but are not limited thereto.

Preferably, the linker conjugating the antibody or a fragment thereof with the aptamer may be a chemical linker. The pincer according to the present invention is characterized by including an antibody or an aptamer which specifically binds to different binding sites of the same target material. Therefore, it is preferable for the antibody and aptamer to maintain appropriate length, and this can be achieved by linking them by the linker. If the linker is too short, the relative movement or motion of the antibody or a fragment thereof and the aptamer is constrained and they cannot bind to the same molecule, but rather bind to different molecules, thereby failing to provide a significant increase in binding affinity expected when using the pincer according to the present invention. Meanwhile, if the linker is too long, it can be problematic as the movement or motion of the antibody or a fragment thereof and the aptamer becomes independent, and thus they cannot target single molecules, but rather bind different molecules. Therefore, it is important to select the linker with appropriate length. In this light, it is advantageous to use a chemical linker. For example, the length of the linker can be adjusted by inserting polyethylene glycol (PEG), etc. and adjusting the number thereof.

Preferably, the chemical linker binds to an amine group, a carboxyl group, or a sulfhydryl group on the antibody and the aptamer. Therefore, the chemical linker preferably contains functional groups which can form a binding with the amine group, the carboxyl group, or the sulfhydryl group by targeting them.

As used herein, the term "target materials" includes, without limitation, materials to be separated or detected, etc. upon binding with the pincer of the present invention, and the examples thereof include cells, proteins, nucleic acids, compounds, etc. The term may also include, without limitation, materials capable of binding to the antibody or the aptamer designed for the purpose of separation or detection.

In another aspect, the present invention provides a method for preparing the pincer for binding to a target material, wherein an antibody or a fragment thereof binding to a first target site of the target material and an aptamer binding to a second target site of the target material are conjugated via a linker, comprising: preparing an antibody or a fragment thereof conjugated to a first linker and an aptamer conjugated to a second linker; and conjugating the antibody and the aptamer conjugated to the linkers via a covalent bond.

The pincer molecule, the antibody, a fragment thereof, the aptamer, and the linker are the same as described above.

Preferably, the antibody and the aptamer linked to the linker may be formed by addition, condensation, or substitution of a cross-linking agent via the amine group, the carboxyl group, or the sulfhydryl group on the antibody and the aptamer.

Preferably, the cross-linking agent may be a compound comprising functional groups selected from the group consisting of carbodiimide, N-hydroxysuccinimide ester (NHS ester), imidoester, pentafluorophenyl ester, hydroxymethyl phosphine, maleimide, haloacetyl, pyridyldisulfide, thiosulfonate, and vinylsulfone for binding to the antibody or aptamer, and the functional group is preferably selected according to the type of a functional group on the antibody or the aptamer through which the binding occurs.

The non-limiting examples of the cross-linking agent may include 1-ethyl-3-(3-dimethylaminopropyl) carbodiimide (EDC), N,N'-dicyclohexylcarbodiimide (DCC), succinimidyl acetylthioacetate (SATA), sulfosuccinimidyl-4-(N-D-maleimidomethyl)cyclohexane-1-carboxylate (sulfo-SMCC), dimethyl adipimidate-2HCl (DMA), dimethyl pimelimidate-2HCl (DMP), dimethyl suberimidate-2HCl (DMS), dimethyl 3,3'-dithiobispropionimidate-2HCl (DTBP), sulfosuccinimidyl (4-iodoacetyl)aminobenzoate (sulfo-SIAB), succinimidyl (4-iodoacetyl)aminobenzoate (SIAB), succinimidyl 3-(bromoacetamido)propionate (SBAP), succinimidyl iodoacetate (STA), succinimidyl-([N-maleimidopropionamido]-# ethyleneglycol ester (SM(PEG)$_n$, wherein n=2, 4, 6, 8, 12, or 24), succinimidyl-4-(N-D-maleimidomethyl)cyclohexane-1-carboxylate (SMCC), succinimidyl 4-(N-maleimidomethyl)cyclohexane-1-carboxy-(6-amidocaproate) (LC-SMCC), N-ε-maleimidocaproyl-oxysulfosuccinimide ester (sulfo-EMCS), N-ε-maleimidocaproyl-oxysuccinimide ester (EMCS), N-γ-maleimidobutyryl-oxysulfosuccinimide ester (sulfo-GMBS), (N-γ-maleimidobutyryl-oxysuccinimide ester (GMBS), N-κ-maleimidoundecanoyl-oxysulfosuccinimide ester (sulfo-KMUS), m-maleimidobenzoyl-N-hydroxysulfosuccinimide ester (sulfo-MBS), m-maleimidobenzoyl-N-hydroxysuccinimide ester (MBS), sulfosuccinimidyl 4-(p-maleimidophenyl)butyrate (sulfo-SMPB), succinimidyl 4-(p-maleimidophenyl)butyrate (SMPB), N-α-maleimidoacet-oxysuccinimide ester (AMAS), N-β-maleimidopropyl-oxysuccinimide ester (BMPS), succinimidyl 6-[(β-maleimidopropionamido) hexanoate] (SMPH), 2-pyridyldithiol-tetraoxaoctatriacontane-N-hydroxysuccinimide (PEG12-SPDP), PEG4-SPDP, sulfosuccinimidyl 6-[3'-(2-pyridyldithio)propionamido] hexanoate (sulfo-LC-SPDP), succinimidyl 3-(2-pyridyldithio)propionate (SPDP), succinimidyl 6-[3'-(2-pyridyldithio)propionamido]hexanoate (LC-SPDP), 4-succinimidyloxycarbonyl-alpha-methyl-alpha(2-pyridyldithio)toluene (SMPT), disuccinimidyl suberate (DSS), bis(succinimidyl) penta(ethylene glycol) (BS(PEG)$_5$), bis(succinimidyl) nona(ethylene glycol) (BS(PEG)$_9$), bis[sulfosuccinimidyl] suberate (BS3), bis[2-(succinimidooxycarbonyloxy)ethyl]sulfone (BSOCOES), 3-(2-pyridyldithio)propionyl hydrazide (PDPH), disuccinimidyl glutarate (DSG), dithiobis[succinimidyl propionate] (DSP), 1,8-bismaleimido-# ethyleneglycol, where n=2 or 3 (BM(PEG)$_n$), 1,4-bismaleimidobutane) (BMB), 1,4-bismaleimidyl-2,3-dihydroxybutane (BMDB), bismaleimidohexane (BMH), bismaleimidoethane BMOE, dithiobismaleimidoethane (DTME), tris(2-maleimidoethyl)amine (TMEA), disuccinimidyl suberate (DSS), disuccinimidyl tartarate (DST), 3,3'-dithiobis[sulfosuccinimidylpropionate] (DTSSP), ethylene glycol bis[succinimidylsuccinate] (EGS), ethylene glycol bis[sulfosuccinimidylsuccinate] (sulfo-EGS), tris-succinimidyl aminotriacetate (TSAT), 1,5-difluoro-2,4-dinitrobenzene (DFDNB).

Preferably, the first and second linkers may further include functional groups capable of binding each other in order to form a molecule in the form of a pincer, in addition to conjugation of the antibody and a fragment thereof with the aptamer.

Herein, the functional groups capable of binding to each other may be a thiol group and unsaturated carbon bond, but is not limited thereto.

Therefore, the method may further include introducing a thiol group to any one of the first linker or the second linker.

In specific Examples of the present invention, an antithrombin antibody and an aptamer each containing a primary amine group were used as functional groups. In order to facilitate the binding of the antibody and the aptamer to the linker, a cross-linking agent containing N-acetyl succinimide, which is capable of forming a binding by targeting the amine group, was used such that the linker may bind thereto by a condensation reaction in which N-hydroxysuccinimide (NHS) is eliminated. Herein, the cross-linking agent reacted with the aptamer contains a maleimido group, and the cross-linking agent reacted with the antibody contains an acetylthio group, and therefore, the aptamer conjugated to the linker containing the maleimido group and the antibody conjugated to the linker containing the acetylthio group were formed. Herein, due to double bonds in the acetylthio group and the maleimido group, a direct addition reaction was difficult to perform. Thus, the antibody conjugated to the linker containing the acetylthio group at the end was first reacted with $NH_2OH$ to covert the acetylthio group into a thiol group, and accordingly, the antibody conjugated to the linker containing the thiol group formed at the end was reacted with the aptamer conjugated with the linker containing the maleimido group at 37° C. for 0.5 hours to 1 hour, and subsequently at 4° C. overnight to obtain an antibody-aptamer pincer in which the antibody and the aptamer are conjugated via the double bond between the thiol group and the maleimido group.

In still another aspect, the present invention provides a method for preparing the pincer for binding to a target material, wherein an antibody or a fragment thereof binding to a first target site of the target material and an aptamer binding to a second target site of the target material are conjugated via a linker, comprising reacting a cross-linking agent comprising a first functional group at one end and a second functional group at another end with the antibody and the aptamer.

The pincer, the antibody, a fragment thereof, the aptamer, the linker, and the cross-linking agent are the same as described above. Also, the functional groups on the antibody or a fragment thereof, the aptamer and the cross-linking agent for cross-linking, and the conjugation thereof are the same as described above.

The first functional group and the second functional group may be the same or different. More preferably, different functional groups may be used for the ease of reaction. When the first functional group is different from the second functional group, one end of the cross-linking agent can bind to the aptamer and another end thereof can specifically bind to the antibody through each functional group, which enables formation of the pincer via a one-pot reaction. Whereas, when the first functional group is same as the second functional group, the functional group is first reacted with one of the antibody or a fragment thereof, or the aptamer, and subsequently reacted with the other in sequence, thereby preparing the pincer. Herein, the reaction can be performed by adjusting the concentration ratio between the cross-linking agent and the antibody or a fragment thereof, or the aptamer, whichever reacts first, to be 1:1, that is, by adjusting the reaction such that the binding can only occur with one of the two functional groups on the same cross-linking agent.

As such, the reactions between the cross-linking agent, and the antibody and the aptamer may be carried out simultaneously or in sequence. If the reactions are carried out in sequence, the order of the reactions is insignificant.

In still another aspect, the present invention provides a composition for detecting or separating a target material comprising the pincer for binding to a target material, wherein an antibody or a fragment thereof binding to a first target site of the target material and an aptamer binding to a second target site of the target material are conjugated via a linker.

The pincer, the antibody, a fragment thereof, the aptamer, and the linker are the same as described above.

The pincer can be used to detect and separate target materials such as cells, proteins, nucleic acids, compounds, etc. Preferably, the composition according to the present invention can be used to detect or separate antigens as a target material.

In still another aspect, the present invention provides a kit for detecting or separating a target material including the composition for detecting and separating the target material.

As used herein, the term "detection" refers to an activity for determining the presence of a target material in a sample, and the term "separation" refers to an activity of selectively selecting a target material in a mixed sample.

Preferably, the composition for detecting or separating a target material according to the present invention can be provided in the form of a biochip by fixing onto a substrate, or in the form of a column filled with the composition, but is not limited thereto.

In still another aspect, the present invention provides a method for detecting or separating a target material, comprising bringing the composition into contact with a sample comprising the target material.

As used herein, the term "sample" includes samples such as tissues, cells, whole blood, serum, plasma, saliva, sputum, cerebrospinal fluid, or urine, which are expected to contain a target material to be detected, but is not limited thereto.

The method for detecting or separating the target material according to the present invention may further include staining the target material in a sample with a fluorescent substance, etc. in order to facilitate measurement and enable quantitative analysis.

In still another aspect, the present invention provides a drug carrier comprising the pincer for binding to a target material, wherein an aptamer conjugated to a second target site of the pincer loads the drug.

The drug may be loaded by a method known in the art. The drug which is conjugated to the aptamer in the drug carrier is not specifically limited, but may be a drug to be specifically carried to the target material. Examples of the drug may include chemical drugs, biopharmaceuticals, etc. The chemical drugs may include anti-inflammatory agents, analgesics, anti-arthritic agents, antispasmodics, anti-depression agents, antipsychotics, sedatives, anxiolytics, drug antagonists, anti-Parkinson's disease drugs, cholinergic agonists, anticancer agents, anti-angiogenic agents, immunosuppressants, immuno stimulants, antiviral agents, antibiotics, appetite suppressants, anticholinergics, antihistamines, antimigraine agents, hormonal agents, coronary vessels, cerebral or peripheral vasodilators, contraceptives, anti-thrombotic agents, diuretics, antihypertensive agents, cardiovascular agents, diagnostic agents, cosmetic ingredients (for example, antiwrinkle agents, aging inhibitors, and skin whitening agents), etc., but are not limited thereto.

According to a preferred embodiment, the drug is an anticancer agent.

The conjugation between the drug and the aptamer in the drug carrier can be achieved via a covalent bond or a non-covalent bond, and the drug can be non-covalently conjugated to the structure of the aptamer by intercalation. Since the aptamer is an oligonucleotide molecule, there are base-stacking interactions between the bases, which are components of the aptamer, and the drug diffuses into the stacked bases by intercalation.

In one embodiment of the present invention, it was confirmed that an AAP-HER2-Dox complex, wherein doxorubicin (Dox) is inserted into the DNA double helix structure of an anti-HER2 aptamer, shows a significantly higher cell death of SK-BR-3, which is a cancer cell, compared to Dox alone, an aptamer-Dox, and an antibody-Dox, which in turn significantly increases the affinity of the drug carrier for the target molecule, and thus, it was predicted that the complex can show an effective therapeutic effect by delivering the drug only into the desired target. Therefore, the complex can be used in an innovative drug delivery and release system.

In still another aspect, the present invention provides a use of the target-specific binding of the pincer or the drug carrier.

BEST MODE

Hereinafter, the present invention will be described in more detail with reference to the following examples. However, the following examples are provided for illustrative purposes only, and the scope of the present invention should not be limited thereto in any manner.

Example 1: Materials

A 15-mer (SEQ ID NO. 1; 5'-H₂N—(CH₂)₆-GGT TGG TGT GGT TGG-3') and a 29-mer (SEQ ID NO. 2; 5'-H₂N—(CH₂)₆-AGT CCG TGG TAG GGC AGG TTG GGG TGA CT-3'), which specifically bind to thrombin, and an anti-human epidermal growth factor 2 (HER2) antibody (SEQ ID NO: 3; 5'-H₂N—(CH₂)₆-AACCG CCCAA ATCCC TAAGA GTCTG CACTT GTCAT TTTGT ATATG TATTT GGTTT TTGGC TCTCA CAGAC ACACT ACACA CGCAC A-3'), which specifically binds to HER2, were purchased from Bioneers. Thrombin and anti-thrombin antibody (F-1), which specifically bind thereto, were purchased from Research Laboratories and Santa Cruz Biotech, respectively. In addition, 5(6)-FAM and SE(5-(and-6)-carboxyfluorescein, succinimidyl ester) were purchased from ANA SPEC. UV absorbance was measured using an 8453 UV-visible spectrophotometer, and fluorescence spectra were measured using a Synergy MX fluorescence spectrophotometer. All experiments were run three times.

Example 2: Conjugation of Thrombin Aptamer with Thrombin Antibody 2.1. Conjugation of a Thrombin Aptamer with a Cross-Linker

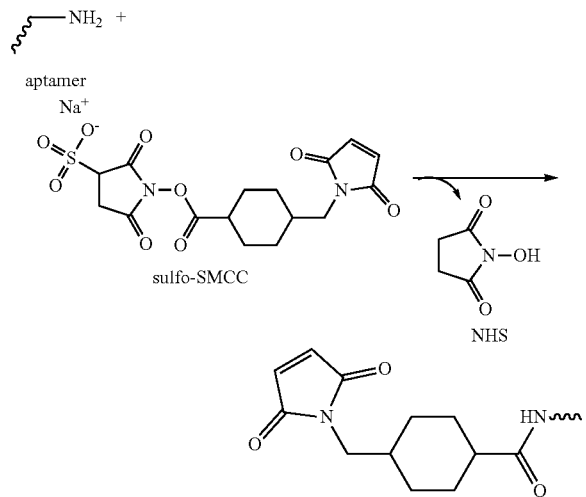

15 μL (1.5 nmol) of 15-mer and 29-mer DNA aptamer solutions, which specifically bind to thrombin, were prepared and added to 350 μL of buffer solution A (pH 7.2; 0.1 M sodium phosphate and 0.15 M sodium chloride). 60 μL of sulfosuccinimidyl-4-(N-maleimidomethyl)cyclohexane-1-carboxylate (sulfo-SMCC) solution prepared at a concentration of 250 μM was added to the aptamer solution above (mole ratio of sulfo-SMCC:aptamer=10:1) and the resultant was reacted at room temperature. The reactant was centrifuged using a 3 k amicon. Buffer solution A was used as a solvent. The centrifugation was performed eight times at 13,000 rpm for 30 minutes each, and the resultant was lyophilized and stored.

2.2. Conjugation of an Anti-Thrombin Antibody with a Cross-Linker

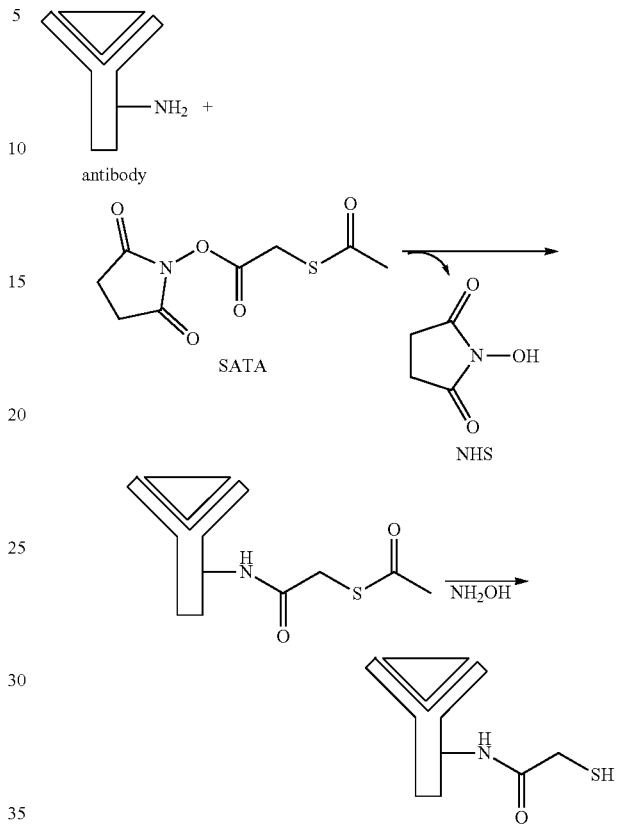

225 μL (300 pmol) of a solution containing the anti-thrombin antibody, which specifically binds to thrombin, was prepared and added to 300 μL of buffer solution B (pH 7.2; 0.1 M sodium phosphate, 0.15 M sodium chloride, and 0.01 M EDTA). 12 μL of sulfosuccinimidyl acetyl thioacetate (SATA) prepared at a concentration of 250 μM was added to the antibody solution (mole ratio of SATA:antibody=10:1), and the resultant was reacted at room temperature for 2 hours. 1.65 g of NH₂OH, 1.20 g of sodium phosphate, and 0.327 g of EDTA were dissolved in 100 mL of distilled water to prepare a solution of pH 7.2 containing 0.5 M NH₂OH, 0.1 M sodium phosphate, and 0.01 M EDTA. 300 μL of NH₂OH solution was added to the reactant, and the resultant was reacted at room temperature for 2 hours. The reaction solution was centrifuged using a 3 k amicon. Herein, buffer solution C (pH 7.2; 0.1 M sodium phosphate, 0.1 M NaCl, and 0.01 M EDTA) was used as a solvent. The centrifugation was performed eight times at 10,000 rpm for 30 minutes, and the resultant was stored at 4° C.

2.3. Conjugation of the Anti-Thrombin Antibody with the Aptamer

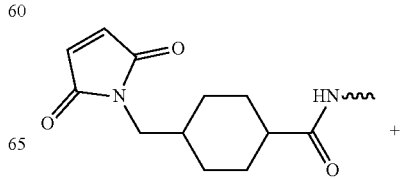

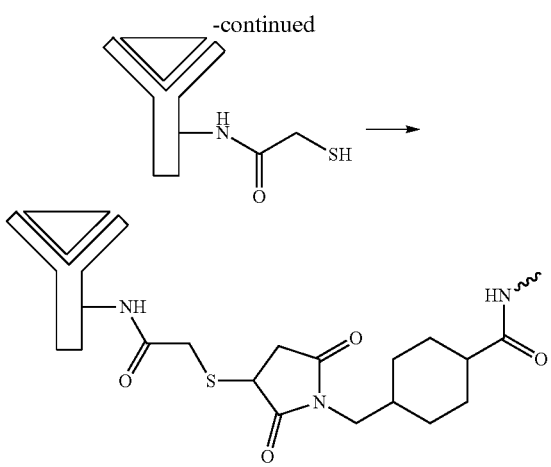

The products obtained from Examples 2.1 and 2.2 were mixed and reacted at 37° C. for 30 to 60 minutes. Thereafter, the resultant was reacted at 4° C. overnight. The reaction solution was centrifuged using a 30 k amicon. Buffer solution C was used as a solvent, and the centrifugation was performed eight times at 10,000 rpm for 30 minutes each. The product was stored at 4° C.

FIG. 2 shows UV absorption spectra of the thrombin aptamer conjugated to the anti-thrombin antibodies, and specifically, it shows UV absorption spectra of (a) the anti-thrombin antibody conjugated to a thrombin 15-mer aptamer (AAP-15) and (b) the anti-thrombin antibody conjugated to an anti-thrombin 29-mer aptamer (AAP-29).

Preparation Example 1: Conjugation of Thrombin with FAM

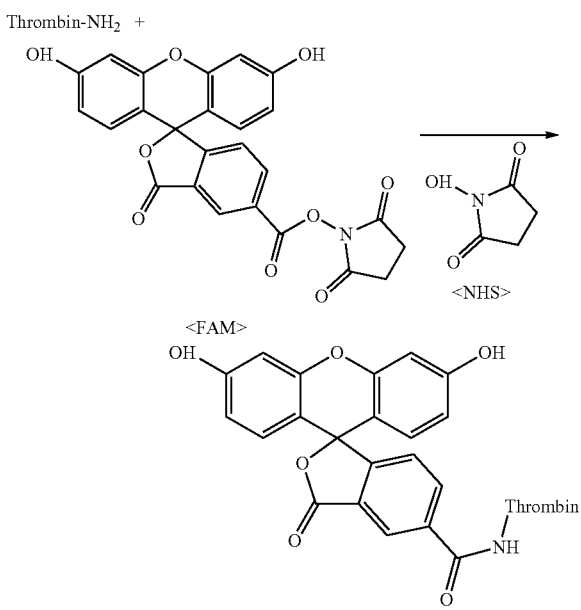

200 μL (2 nmol) of the thrombin solution prepared at a concentration of 10 pmol/pt was prepared. 500 μL of the buffer solution (pH 8.3), in which PBS buffer solution (pH 7.0) and NaHCO₃ (pH 9.0) were mixed in a ratio of 20:1, was added to the thrombin solution. 4 μL (2 nmol) of FAM solution prepared at a concentration of 500 μM was added thereto, and the resultant was reacted for 3 hours. The reaction solution was centrifuged using a 30 k amicon. The buffer solution was used as a solvent, the centrifugation was repeated for eight times at 10,000 rpm for 30 minutes each, and the product was lyophilized and stored. The UV absorbance for the product was measured and quantified. FIG. 3 shows UV absorption spectra, and the result of FAM-labeled thrombin (508 nM) is shown in FIG. 3a.

Preparation Example 2: Conjugation of Bovine Serum Albumin with FAM

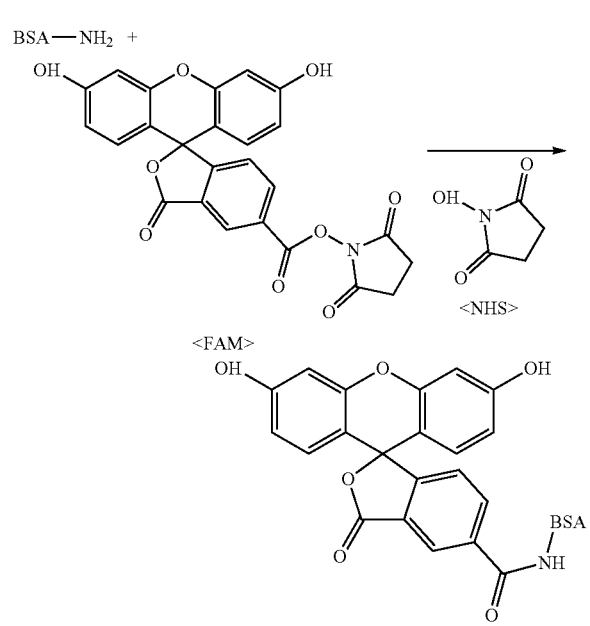

As a control group, bovine serum albumin (BSA), which non-specifically binds to the anti-thrombin antibody and/or the thrombin aptamer, was used instead of thrombin. For quantification, BSA was labeled with FAM as in Preparation Example 1. Specifically, 103.8 μL of BSA solution (3 nmol) was prepared. 500 μL of the buffer solution (pH 8.3), in which PBS buffer solution (pH 7.0) and NaHCO₃ (pH 9.0) were mixed in a ratio of 20:1, was added to the BSA solution. 6 μL (3 nmol) of FAM solution prepared at a concentration of 500 μM was added thereto, and the resultant was reacted for 3 hours. The reaction solution was centrifuged using a 30 k amicon. The mixed buffer solution was used as a solvent, the centrifugation was repeated for eight times at 10,000 rpm for 30 minutes each, and the product was lyophilized and stored. The UV absorbance for the product was measured and quantified. FIG. 3 shows UV absorption spectra, and the result of FAM-labeled BSA (52.632 μM) is shown in FIG. 3b.

Example 3: Measurement of the Binding Affinity of the Pincer Using Dialysis

The binding affinity of the pincer, which was prepared by conjugating the thrombin aptamer and the anti-thrombin antibody via the chemical linker, for thrombin was measured using dialysis. Specifically, a measuring device was filled with 10% ethanol using a 1 to 200 μL micropipette tip, and then allowed to stand for 10 minutes in the same ethanol solution. Thereafter, the ethanol was fully removed from the measuring device. Likewise, the device was again filled with deionized water using a 1 to 200 μL micropipette tip, and then allowed to stand for 15 to 20 minutes in the same deionized water. The deionized water was fully removed, and the 15-mer aptamer-antibody pincer or the 29-mer aptamer-antibody pincer prepared in Example 2, and the thrombin-FAM prepared according to Preparation Example 1 were placed in the device, and PBS solution was added until the total volume was 1 mL. 100 mL of PBS buffer solution was used as an external buffer solution. The device was immersed in the buffer solution, and the solution was stirred for about 24 hours using a magnetic bar while being kept at room temperature to allow the solution to reach equilibrium. Fluorescence was measured using 200 μL of the external solution for quantitative measurement. Also, the pincer according to the present invention was reacted with FAM-labeled BSA instead of thrombin, and it was used as a control group. The concentration of thrombin or BSA reacted was varied within the sub-nanomole levels (approx. 1 nM) to derive the fraction of the bound thrombin for thrombin (or BSA) that binds to the pincer, according to the concentration of the target material, and the results were illustrated in FIGS. 4 and 5. Herein, the 15-mer and 29-mer DNA were used as thrombin aptamers, and each result thereof was illustrated in FIGS. 4 and 5.

As shown in FIG. 4, the antibody-aptamer pincer (AAP), in which the anti-thrombin antibody and the 15-mer thrombin aptamer is conjugated, showed $K_d^{app}$ value (dissociation constant) of 567 pM for thrombin. Meanwhile, as shown in FIG. 5, the AAP including the 29-mer aptamer showed two $K_d^{app}$ values of 64.5 pM and 101 pM, confirming that the AAP binds to thrombin in a biphasic mode. In contrast, the binding affinity of the two types of pincers for BSA was insignificant. This implies that the binding affinity of the pincer according to the present invention was increased by 35- to 775-fold compared to reactions with the antibody or the aptamer alone, considering that $K_d^{app}$ values of the anti-thrombin antibody, the 15-mer DNA aptamer, and the 29-mer DNA aptamer are 50 nM, 20.2 nM, and 3.5 nM, respectively, which is reported in the art. Also, considering the results of BSA, it was confirmed that the pincer according to the present invention showed a significantly high specificity for the target material.

Example 4: Conjugation of HER2 Aptamer with HER2 Antibody

The conjugation of a HER2 aptamer and a HER2 antibody was prepared in the same manner as the conjugation of the thrombin aptamer and the thrombin antibody.

Example 4.1: Conjugation of a HER2 Aptamer and a Cross-Linker

The conjugation of the HER2 aptamer and the cross-linker was prepared in the same manner as the conjugation of the thrombin-aptamer and the cross-linker, and the anti-human epidermal growth factor 2 (HER2) aptamer (SEQ ID NO: 3: 5'-H2N—(CH2)6-AACCG CCCAA ATCCC TAAGA GTCTG CACTT GTCAT TTTGT ATATG TATTT GGTTT TTGGC TCTCA CAGAC ACACT ACACA CGCAC A-3'), which specifically binds to HER2, was purchased from Bioneers.

1.0 nmol of a solution containing HER2 aptamers, which specifically bind to HER2, was prepared and added to 350 μL of buffer solution A (pH 7.2; 0.1 M sodium phosphate and 0.15 M sodium chloride). 60 μL of sulfosuccinimidyl-4-(N-maleimidomethyl)cyclohexane-1-carboxylate (sulfo-SMCC) solution prepared at a concentration of 250 μM was added to the aptamer solution above (mole ratio of sulfo-SMCC:aptamer=10:1), and the resultant was reacted at room temperature. The reactant was centrifuged using a 3 k amicon. Buffer solution A was used as a solvent. The centrifugation was performed eight times at 13,000 rpm for 30 minutes each, and the product was lyophilized and stored.

Example 4.2: Conjugation of a HER2 Antibody with a Cross-Linker 200 pmol of a solution containing the anti-HER2 antibody, which specifically binds to HER2, was prepared and added to 300 μL of buffer solution B (pH 7.2; 0.1 M sodium phosphate, 0.15 M sodium chloride, and 0.01 M EDTA). 12 μL of sulfosuccinimidyl acetyl thioacetate (SATA) prepared at a concentration of 250 μM was added to the antibody solution (mole ratio of SATA:antibody=10:1), and the resultant was reacted at room temperature for 2 hours. 1.65 g of $NH_2OH$, 1.20 g of sodium phosphate, and 0.327 g of EDTA were dissolved in 100 mL of distilled water to prepare a solution of pH 7.2 containing 0.5 M $NH_2OH$, 0.1 M sodium phosphate, and 0.01 M EDTA. 300 μL of the $NH_2OH$ solution prepared was added to the reactant, and the resultant was reacted at room temperature for 2 hours. The reaction solution was centrifuged using a 3 k amicon. Herein, buffer solution C (pH 7.2; 0.1 M sodium phosphate, 0.1 M NaCl, and 0.01 M EDTA) was used as a solvent. The centrifugation was performed eight times at 10,000 rpm for 30 minutes each, and the product was stored at 4° C.

4.3. Conjugation of the Anti-HER2 Antibody with the HER2 Aptamer

The products obtained from Examples 4.1 and 4.2 were mixed and reacted at 37° C. for 30 to 60 minutes. Thereafter, the resultant was reacted at 4° C. overnight. The reaction solution was centrifuged using a 30 k amicon. Buffer solution C was used as a solvent, and the centrifugation was performed eight times at 10,000 rpm for 30 minutes each. The product was stored at 4° C.

Example 5: Preparation of Dox-Loaded AAP-HER2-Dox, Aptamer-Dox, and Antibody-Dox Based on the aptamers in which the antibody and the drug are loaded, it was examined whether the AAP system could be applicable to DDS, which targets HER2.

In order to form AAP-HER2, the anti-HER2 aptamer in Example 4 was conjugated to the anti-HER2 antibody (monoclonal antibody N12) and Dox (doxorubicin) was conjugated to the DNA structure of the anti-HER2 aptamer to be formulated (hereinafter, assigned Dox-loaded AAP-HER2 or AAP-HER2-Dox). Such method was prepared according to Liu (Liu et al. *Journal of Translational Medicine* 2012, 10:148), etc.

FIG. 6 shows UV absorption spectra of (a) the anti-HER2 antibody conjugated with the anti-HER2 aptamer, (b) the anti-HER2 antibody conjugated with the anti-thrombin 29-mer aptamer, (c) the anti-HER2 antibody conjugated with single-stranded DNA 1 (ssDNA1), and (d) the anti-HER2 antibody (9G6) conjugated with the anti-HER2 aptamer. In FIG. 6, the anti-HER2 monoclonal antibody (N12) was covalently bonded to each of the anti-thrombin 29-mer aptamer and ssDNA1 as a negative control group.

Also, the anti-HER2 monoclonal antibody (9G6, Thermo) is known not to be effective in killing compared to the anti-HER2 antibody (N12), and thus was used as another negative control group by conjugating to the anti-HER2 aptamer.

The anti-HER2 aptamer has two recognition sites, and thus can bind to a HER2 epitope peptide having Kd of 18.9 nM or to the extracellular domain of a HER2 protein having Kd of 315 nM. Meanwhile, the epitope of the anti-HER2 antibody is located at C531-A586, and the anti-HER2 antibody can inhibit the growth of HER2-positive tumor cells independently. Further, the two binding sites of the AAP-HER2 or AAP-HER2-Dox can each recognize different parts of HER2 molecules, and the growth of tumor cells including HER2 can be specifically inhibited by the anti-HER2 antibody and Dox.

The formation of the AAP-HER2-Dox complex was confirmed based on the fact that once fluorescent doxorubicin (Dox) was inserted into the DNA double helix structure via intercalation, it could be quenched.

FIG. 7 shows fluorescence spectrum analyses of the anti-HER2 aptamer and the anti-HER2 antibody in the presence of Dox: (a) shows preparation of Dox solutions of varying concentrations by increasing the mole ratio of Dox (from bottom to top: 0.5, 1, 4, 10, 50, and 100) while fixing the concentration of the anti-HER2 aptamer; (b) shows fluorescence intensity when the mole ratio of Dox/anti-HER2 aptamer is 10; (c) shows preparation of Dox solutions of varying concentrations by increasing the mole ratio of Dox (from bottom to top: 1, 2, and 4) while fixing the concentration of the anti-HER2 antibody; and (d) shows fluorescence intensity when Dox (5 nmol) is used alone (top), when the anti-thrombin 29-mer aptamer is mixed at 50 nmol (middle), and when ssDNA1 is mixed at 50 nmol (bottom), and these were used as negative control groups. The fluorescence spectra of doxorubicin were measured using a Synergy MX fluorescence spectrophotometer.

Through the results shown in FIG. 7, the anti-HER2 aptamer can be loaded into Dox, and it was confirmed that the fluorescence intensity was the highest when the molar ratio of the aptamer and Dox was 1:10 (FIG. 7). Also, Dox could be effectively inserted into the anti-HER2 aptamer compared to single-stranded DNA1 or the anti-thrombin 29-mer aptamer (the sequences of ssDNA1 and scrambled DNA were used as negative control groups) (FIG. 7D).

Example 6: Evaluation of Dox Release from Dox-Loaded Anti-HER2 Aptamer in the Presence of Epitope When the molar ratio of Dox was fixed at 10, various concentrations of HER2 epitope solutions were mixed with 250 nM of the anti-HER2 aptamer, and the Dox-loaded anti-HER2 aptamer solutions of varying concentrations were mixed with 250 nM of the HER2 epitope peptide. The fluorescence spectra of doxorubicin (Dox) were measured using a Synergy MX fluorescence spectrophotometer.

In order to confirm whether the presence of HER2 has an effect on the modification of the folding states of the Dox-loaded anti-HER2 aptamer and the drug release, fluorescence spectrum analyses were conducted (FIG. 8). FIG. 8 shows fluorescence spectrum analyses of the Dox-loaded anti-HER2 aptamer in the presence of HER2 epitope peptides: (a) HER2 epitope solutions of varying concentrations were mixed with 250 nM of the anti-HER2 aptamer when the molar ratio of Dox was fixed at 10; and (b) various concentrations of the Dox-loaded anti-HER2 aptamer were mixed with 250 nM of the HER2 epitope peptides when the molar ratio of Dox was fixed at 10, and each fluorescence spectrum was obtained after 0.5 hours (empty circle) and 6 hours (filled circle), respectively.

As a result, the binding event between the Dox-loaded anti-HER2 aptamer and the HER2 epitope modified the folding of the anti-HER2 aptamer and induced the release of inserted Dox. The $K_d^{app}$ (apparent dissociation constant) between the Dox-loaded anti-HER2 aptamer and the HER2 epitope was about 50 nM, and the Kd value reported for the Dox-loaded anti-HER2 aptamer and the HER2 epitope was 18.9 nM. With the comparison above, it can be implied that the insertion of Dox can induce a partial modification of the folding state of the anti-HER2 aptamer.

Example 7: Measurement of Cell Viability

Example 7.1: Measurement of the Viability of Breast Cancer Cells of AAP-HER2-Dox According to the Concentrations SK-BR-3, MDA-MB-453, and MCF-7 human breast cancer cells were obtained from ATCC, and these cells were maintained in tissue culture plates with RPMI-1640 medium containing 2 mM L-glutamine, 10% fetal bovine serum, 100 IU/mL penicillin, and 0.1 mg/mL streptomycin, under an atmosphere of 5% $CO_2$ at 37° C. In order to maintain the cells in the log phase, a fresh medium was resupplied two or three times a week.

The cell viability was measured using the standard 3-(4, 5-dimethylthiazol-2-yl)-2,5-diphenyltetrazolium bromide (MTT) reduction assay. Simply, cells that grow exponentially were inoculated at a density of $5\times10^3$ per well in a 96-well with flat bottom plate (200 μL/well) and cultured at 37° C. for 24 hours. Thereafter, each of the AAP-HER2-Dox, the antibody-Dox, the aptamer-Dox, Dox, the anti-HER2 antibody, and the anti-HER2 aptamer were exposed to different concentrations for 24 hours.

10 μL of MTT solution was added to each well, and the cells were further cultured at 37° C. for 4 hours. The amount of formazan product was measured at 570 nm. The cell survival fraction was calculated as a percentage of the untreated control group. The experimental data shows that the corresponding $IC_{50}$ values were calculated and that the values were introduced into a dose-response curve to obtain a theoretical curve using a non-linear regression analysis. Fluorescence was analyzed using an Axio Observer Z1 inverted microscope (Carl Zeiss Inc., USA).

FIG. 9a shows the effect of the AAP-HER2-Dox on the viability of SK-BR-3, MDA-MB-453, and MCF-7 cells. FIG. 9b shows concentration-dependent cell viability for SK-BR-3 on the AAP-HER2-Dox, the antibody-Dox, the aptamer-Dox, and Dox.

It was confirmed through FIG. 9a that the AAP-HER2-Dox could inhibit the cell survival at different levels after 24 hours. Specifically, the $IC_{50}$ values of the AAP-HER2-Dox obtained for SK-BR-3, MDA-MB-453, and MCF-7 were 15.5 nM, 35.0 nM, and 83.4 nM, respectively. Such results are consistent with the cell expression levels of HER2, indicating that the AAP-HER2-Dox can distinguish target cells from non-target cells and that HER2 can be used as a specific DDS for cancer cells with over-expressed HER2.

The SK-BR-3 cells having a high expression level for HER2 were selected in the cell membrane and compared with the AAP-HER2-Dox, thereby exposing the cells to the Dox-mixed anti-HER2 (antibody-Dox) or the Dox-loaded anti-HER2 aptamer (aptamer-Dox).

It was confirmed through FIG. 9b that the cytotoxic effect of the AAP-HER2-Dox was significantly different from that of the antibody-Dox, the aptamer-Dox, or Dox alone in a concentration-dependent manner, and the AAP-HER2-Dox among the four materials showed the highest cytotoxic effect. It is predicted that the $IC_{50}$ values of the AAP-HER2-Dox, the antibody-Dox, and the aptamer-Dox for SK-BR-3 are 15.5 nM, 25.1 nM, 38.6 nM, and 43.9 nM, indicating that the AAP-HER2-Dox shows three times higher cytotoxicity compared to that of Dox.

FIG. 10 shows concentration-dependent cell viability for SK-BR-3 in the presence of the AAP-HER2-Dox, the anti-HER2 antibody, and the anti-HER2-aptamer. The SK-BR-3 cells were exposed to the AAP-HER2-Dox, the anti-HER2 antibody or the anti-HER2-aptamer at a concentration range of 0 nM to 100 nM. Since the molar ratio of Dox/AAP-HER2 to AAP-HER2-Dox is 1:10, the $IC_{50}$ value for the concentration of the antibody at 1.55 nM is equivalent to the $IC_{50}$ value for the concentration of Dox at 15.5 nM.

Although the anti-HER2 aptamer alone does not have cytotoxicity against SK-BR-3 cells (FIG. 10), the aptamer-Dox showed cytotoxicity compared to Dox. In contrast, the cytotoxicity of the antibody-Dos is similar to that of the aptamer-Dox or Dox. Considering that Dox cannot be loaded onto the antibody (FIG. 7) and that the anti-HER2 antibody alone cannot inhibit the growth of HER2-positive tumor cells, such results were found to be interesting.

Example 7.2: Measurement of the Viability of Breast Cancer Cells of AAP-HER2-Dox According to Time It was examined whether the aptamer-Dox and the antibody-Dox substantially increase the cancer-killing effect of Dox. As a result, the cytotoxicities of the aptamer-Dox and the antibody-Dox were measured as a function of incubation time, compared to Dox alone. Also, FIGS. 11 and 12 confirm that the presence of the anti-HER2 aptamer or the antibody increase the cancer-killing effect of Dox in a relatively small amount.

FIG. 11 shows cell viability of SK-BR-3 according to time-dependent incubation of Dox alone (black), the aptamer-Dox (grey), the antibody-Dox (white), and the AAP-HER2-Dox (hatching). The concentrations of the total amount loaded and free Dox were (a) 34 nM and (b) 340 nM, respectively. As a result, the aptamer-Dox, and the antibody-Dox show a higher cancer-killing effect compared to Dox alone, indicating that the presence of the anti-HER2 aptamer or the antibody increases a cancer-killing effect of Dox in a short period.

FIG. 12 shows cell viability of SK-BR-3 according to time-dependent incubation in the presence of (a) Dox alone, (b) the aptamer-Dox, (c) the antibody-Dox, and (d) the AAP-HER2-Dox. The cells were exposed to the total amount loaded and free Dox at a concentration range of 0 nM to 500 nM. As a result, (b) the aptamer-Dox and (c) the antibody-Dox show a higher cancer-killing effect compared to Dox alone, indicating that the presence of the anti-HER2 aptamer or the antibody increases a cancer-killing effect of Dox in a short period.

Example 7.3: Confirmation of Whether the Increased Cytotoxicity of AAP System Depends on Bivalent Recognition and Dox Release In order to confirm whether the increased cytotoxicity of AAP system consisting of three kinds of individual components (e.g., two recognition parts and Dox) is dependent on bivalent recognition and Dox release, control group experiments were performed using three negative control groups of the Dox-loaded anti-thrombin 29-mer aptamer conjugated with the anti-HER2 antibody, the Dox-loaded ssDNA1 (a scramble DNA sequence) conjugated with the anti-HER2 antibody, and the Dox-loaded anti-HER2 aptamer conjugated with the anti-HER2 antibody (9G6). The anti-HER2 antibody (9G6) was selected because the antibody itself is known to have no strong effect in killing, compared to the anti-HER2 antibody (N12).

FIG. 13 shows concentration-dependent cell viability of SK-BR-3 cells in the presence of the AAP-HER2Dox, the Dox-loaded anti-thrombin 29-mer aptamer conjugated with the anti-HER2 antibody, the Dox-loaded ssDNA1 conjugated with the anti-HER2 antibody, the Dox-loaded anti-HER2 aptamer conjugated with the anti-HER2 antibody (9G6), and Dox alone. SK-BR-3 cells were exposed to total amount loaded or free Dox at concentrations of 0 nM, 34 nM, 68 nM, 340 nM, and 510 nM (from left to right).

Specifically, in FIG. 13, although the three negative control groups of the Dox-loaded anti-thrombin 29-mer aptamer conjugated with the anti-HER2 antibody, the Dox-loaded ssDNA1 conjugated with the anti-HER2 antibody, and the Dox-loaded anti-HER2 aptamer conjugated with the anti-HER2 antibody (9G6) show cytotoxicity similar to that of the aptamer-Dox or the antibody-Dox, according to the increased cell-killing effect due to the presence of any one of the anti-HER2 antibody or the aptamer, the increased cytotoxicity induced by any one or two of three individual components was nearly insignificant compared to that induced by AAP-HER2-Dox or Dox alone.

It was observed that the cytotoxicity of the AAP-HER2-Dox was six times higher than that of the anti-HER2 antibody alone (N12 or 9G6) (FIGS. 12 and 13). This signifies that the drug-loaded AAP leads to an increase in cytotoxicity in HER2-overexpressed human cells compared to each component in cell- and concentration-dependent manners. Such results reflect the difference of therapeutic antibody efficacy between drug absorption mechanisms and the antibody-Dox, the aptamer-Dox, and Dox.

Example 8: Evaluation of Intracellular Absorption of Dox

In order to evaluate intracellular absorption of Dox based on fluorescence released by the drug, fluorescence microscopy was employed as depicted in FIGS. 14 and 15. Specifically, it was evaluated whether the AAP-HER2-Dox is effectively taken up by the cells to be used as a DDS for targeting tumor and whether the aptamer part of the complex maintains HER-2 binding capacity during the drug delivery in the DNA structure. As a result, most of the nucleus was stained by the complex in HER2-overexpressed SK-BR-3 breast cancer cells (FIG. 14), thus exhibiting a low $IC_{50}$ as a result.

FIG. 14 shows Dox release from SK-BR-3 cells treated with 100 nM of the aptamer-Dox (column 1), the antibody-Dox (column 2), and the AAP-HER2-Dox (column 3). The nuclei were stained by Hoechst 33258, and the images were confirmed after 4 hours of incubation. As a result, the AAP-HER2-Dox, prepared by the conjugation between the drug-loaded aptamer and the antibody, effectively increased the affinity of the AAP system for the target molecule, and thus can be applied as a platform for targeting DDS against tumors. Such results are consistent with FIG. 11.

FIG. 15 shows a microscopic image illustrating intracellular fluorescence release after 24-hour incubation of SK-BR-3 cells treated with the AAP-HER2-Dox (Dox concentrations of 0 nM, 2.5 nM, and 100 nM) (Column 1: images of phase difference, Column 2: images obtained by a band-pass filter for red fluorescence).

The invention claimed is:

1. A pincer for binding to a target material, comprising an antibody or a fragment thereof binding to a first target site of the target material and an aptamer binding to a second target site of the same target material, wherein the antibody or the fragment thereof and the aptamer are conjugated via a chemical linker; the chemical linker does not contain a peptide component; and the target material is a protein, a nucleic acid, or a compound.

2. The pincer of claim 1, in which the chemical linker conjugating the antibody or the fragment thereof and the aptamer is formed by addition, condensation, or substitution of a cross-linking agent,
   wherein the cross-linking agent is selected from the group consisting of 1-ethyl-3-(3-dimethylaminopropyl) carbodiimide (EDC), N,N'-dicyclohexylcarbodiimide (DCC), succinimidyl acetylthioacetate (SATA), sulfo-succinimidyl-4-(N-D-maleimidomethyl)cyclohexane-1-carboxylate (sulfo-SMCC), dimethyl adipimidate.2HCl (DMA), dimethyl pimelimidate.2HCl (DMP), dimethyl suberimidate.2HCl (DMS), dimethyl 3,3'-dithiobispropionimidate.2HCl (DTBP), sulfosuccinimidyl (4-iodoacetyl)aminobenzoate (sulfo-SIAB), succinimidyl (4-iodoacetyl)aminobenzoate (STAB), succinimidyl 3-(bromoacetamido)propionate (SBAP), succinimidyl iodoacetate (STA), succinimidyl-(N-maleimidopropionamido)-polyethyleneglycol ester (SM (PEG)$_n$, wherein n=2, 4, 6, 8, 12, or 24), succinimidyl-4-(N-D-maleimidomethyl)cyclohexane-1-carboxylate (SMCC), succinimidyl 4-(N-maleimidomethyl)cyclohexane-1-carboxy-(6-amidocaproate) (LC-SMCC), N-ε-maleimidocaproyl-oxysulfosuccinimide ester (sulfo-EMCS), N-ε-maleimidocaproyl-oxysuccinimide ester (EMCS), N-γ-maleimidobutyryl-oxysulfosuccinimide ester (sulfo-GMBS), N-γ-maleimidobutyryl-oxysuccinimide ester (GMBS), N-κ-maleimidoundecanoyl-oxysulfosuccinimide ester (sulfo-KMUS), m-maleimidobenzoyl-N-hydroxysulfosuccinimide ester (sulfo-MBS), m-maleimidobenzoyl-N-hydroxysuccinimide ester (MBS), sulfosuccinimidyl 4-(p-maleimidophenyl)butyrate (sulfo-SMPB), succinimidyl 4-(p-maleimidophenyl)butyrate (SMPB), N-α-maleimidoacet-oxysuccinimide ester (AMAS), N-β-maleimidopropyl-oxysuccinimide ester (BMPS), succinimidyl 6-[(β-maleimidopropionamido)hexanoate] (SMPH), 2-pyridyldithiol-tetraoxaoctatriacontane-N-hydroxysuccinimide (PEG12-SPDP), PEG4-SPDP, sulfosuccinimidyl 6-[3'-(2-pyridyldithio)propionamido]hexanoate (sulfo-LC-SPDP), succinimidyl 3-(2-pyridyldithio)propionate (SPDP), succinimidyl 6-[3'-(2-pyridyldithio)propionamido]hexanoate (LC-SPDP), 4-succinimidyloxycarbonyl-alpha-methyl-alpha(2-pyridyldithio)toluene (SMPT), disuccinimidyl suberate (DSS), bis(succinimidyl) penta(ethylene glycol) (BS(PEG)$_5$), bis(succinimidyl) nona(ethylene glycol) (BS(PEG)$_9$), bis(sulfosuccinimidyl) suberate (BS3), bis[2-(succinimidooxycarbonyloxy)ethyl]sulfone (BSOCOES), 3-(2-pyridyldithio)propionyl hydrazide (PDPH), disuccinimidyl glutarate (DSG), dithiobis(succinimidyl propionate) (DSP), 1,8-bismaleimido-polyethyleneglycol (BM(PEG)$_n$, where n=2 or 3), 1,4-bismaleimidobutane (BMB), 1,4-bismaleimidyl-2,3-dihydroxybutane (BMDB), bismaleimidohexane (BMH), bismaleimidoethane BMOE, dithiobismaleimidoethane (DTME), tris(2-maleimidoethyl)amine (TMEA), disuccinimidyl suberate (DSS), disuccinimidyl tartarate (DST), 3,3'-dithiobis(sulfosuccinimidylpropionate) (DTSSP), ethylene glycol bis(succinimidylsuccinate) (EGS), ethylene glycol bis(sulfosuccinimidylsuccinate) (sulfo-EGS), tris-succinimidyl aminotriacetate (TSAT), and 1,5-difluoro-2,4-dinitrobenzene (DFDNB).

3. The pincer of claim 1, wherein the antibody or the fragment thereof is conjugated to a first additional chemical linker and the aptamer is conjugated to a second additional chemical linker.

4. The pincer of claim 3, wherein the first and second additional chemical linkers further comprise functional groups capable of binding to each other.

5. The pincer of claim 4, wherein the functional groups capable of binding to each other are a thiol group and unsaturated carbon bond.

6. The pincer of claim 1, wherein the chemical linker binds to an amine group, a carboxyl group, or a sulfhydryl group on the antibody and the aptamer.

7. A method for detecting or separating a target material, comprising bringing the pincer of claim 1 into contact with a sample comprising the target material.

8. The method of claim 7, wherein the target material is selected from the group of cells, proteins, nucleic acids, and compounds.

9. A drug carrier comprising the pincer of claim 1, wherein the aptamer of the pincer loads a drug.

10. The drug carrier of claim 9, wherein the drug is doxorubicin.

* * * * *